United States Patent [19]

Hirose et al.

[11] Patent Number: 5,102,895

[45] Date of Patent: Apr. 7, 1992

[54] NOVEL VITAMIN E DERIVATIVES AND PROCESS FOR THE PRODUCTION THEREOF

[75] Inventors: Noriyasu Hirose, Ibaraki; Kimio Hamamura; Takaharu Nakamura, both of Chiba; Kiiti Ema, Tokyo; Takashi Banba, Ibaraki; Tetsuya Nakamura, Tokyo; Hidetoshi Kawashima, Ibaraki; Yuuichi Inai, Tokyo; Noritoshi Sano, Kanagawa; Yuko Miyauchi, Tokyo; Shizumasa Kijima, Chiba, all of Japan

[73] Assignee: Eisai Co., Ltd., Tokyo, Japan

[21] Appl. No.: 636,129

[22] Filed: Dec. 31, 1990

[30] Foreign Application Priority Data

Jan. 5, 1990 [JP] Japan ........................... 2-270

[51] Int. Cl.$^5$ ................. A61K 31/455; C07D 405/14
[52] U.S. Cl. .................... 514/333; 546/256; 549/410
[58] Field of Search .............. 549/410; 546/256; 514/333

[56] References Cited

FOREIGN PATENT DOCUMENTS 0180190 5/1986 European Pat. Off. .

OTHER PUBLICATIONS

Sundaram et al. Lipids, vol. 16, No. 4, pp. 223-227 (1981).
Paul et al., "Effect of Vitamin E on Lipid Components of Atherogenic Rats", Internat. J. Vit. Nutr. Res., vol. 59, pp. 35-39 (1989).

Primary Examiner—Nicky Chan
Attorney, Agent, or Firm—Birch, Stewart, Kolasch & Birch

[57] ABSTRACT

The novel vitamin E derivative provides an excellent antihyperlipemic effect and is defined by the formula (I):

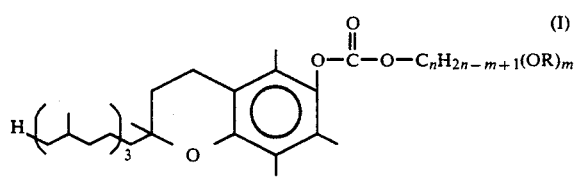

wherein R represents a nicotinoyl group; and m is an integer of from 2 to 5 while n is an integer of from 3 to 6, provided that n is larger than m.

3 Claims, 1 Drawing Sheet

NOVEL VITAMIN E DERIVATIVES AND PROCESS FOR THE PRODUCTION THEREOF

BACKGROUND OF THE INVENTION

1. Field of the Application

This invention relates to novel vitamin E derivatives having excellent effects as a drug and a process for the production thereof.

This invention provides a pharmaceutical composition comprising a pharmacologically effective amount of the vitamin E derivative and a pharmacologically acceptable carrier.

Besides the invention provides a method for treating arteriosclerosis by administering a pharmacologically effective amount of the vitamin E derivative to a human patient.

2. Description of Related Art

It has been known that the administration of nicotinic acid to man serves to lower the blood triglyceride level and the blood cholesterol level. Thus the administration of nicotinic acid has been widely employed in the treatment of hyperlipemia.

However the administration of nicotinic acid per se is not necessarily a convenient therapeutic method, since a rapid increase in the blood nicotinic acid level would cause some side effects.

There has been frequently attempted to develop a novel nicotinic acid derivative which maintains the excellent antihyperlipemic effect of nicotinic acid and scarcely exerts any side effect. For example, α-tocopheryl nicotinate, which is obtained by binding vitamin E to nicotinic acid via an ester bond and shows synergistic effects of vitamin E and nicotinic acid (for example, improving lipid metabolism and promoting microcirculation), has been frequently used clinically. Further, there have been developed nicotinates of polyhydric alcohols such as pentaerythritol tetranicotinate and 2,2,6,6-tetrakis(nicotinoyloxymethyl)cyclohexyl nicotinate.

However none of these compounds is satisfactory in, for example, lowering the blood lipid level. It has been urgently required, therefore, to develop a compound which can more continuously maintain a stable blood nicotinic acid level and scarcely shows any side effect seemingly caused by a rapid increase in the blood nicotinic acid level.

SUMMARY OF THE INVENTION

Under these circumstances, the present inventors have conducted extensive studies. As a result, they have found out that novel vitamin E derivatives, wherein a number of nicotinic acid molecules having an excellent antihyperlipemic effect are bonded to vitamin E via a polyhydroxylalkyloxycarbonyl group, represented by the following general formula (I):

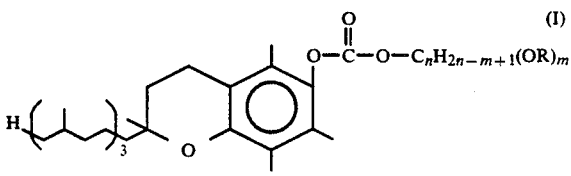

wherein R represents a nicotinoyl group; and m is an integer of from 2 to 5 while n is an integer of from 3 to 6, provided that n is larger than m; namely, nitinoyloxyalkyl 2,5,7,8-tetramethyl-2-(4′,8′,12′-trimethyltridecyl)-6-chromanyl carbonates are enzymatically or nonenzymatically hydrolyzed in the digestive tract or after being absorbed thereinto slowly and continuously, without releasing a large amount of nicotinic acid at once, to thereby maintain the required blood nicotinic acid level for a prolonged period, thus exerting an excellent effect of lowering the blood lipid level. The present invention has been accomplished based on this finding.

In the above general formula (I), the group represented by $-C_nH_{2n-m+1}(OR)_m$ means a straight-chain or branched lower alkyl group having 3 to 6 carbon atoms substituted with $-(OR)_m$ groups. More particularly, 2 to 5 —OR groups (namely, nicotinoyloxy groups) are bonded to the same or different carbon atoms constituting the lower alkyl group having 3 to 6 carbon atoms.

Vitamin E per se, which is one of the members constructing the present invention, also shows an effect of lowering blood lipid level [Paul et al., International Journal of Nutrition and Research, 59, 35–39 (1989)]. It is further known that HDL-cholesterol, which has attracted public attention as a favorable cholesterol, can be increased by administering vitamin E [Sundaram et al., Lipids, 16, 223–227 (1981)].

It has been confirmed that the compounds of the present invention slowly release nicotinic acid when administered orally and that vitamin E, which is another component, is simultaneously hydrolyzed and thus migrates into the plasma. It is therefore expected that the compounds of the present invention exert a synergistic antihyperlipemic effect, since they maintain the antihyperlipemic effect of nicotinic acid while relieving the undesirable properties of nicotinic acid and vitamin E, i.e., another component thereof migrates into the plasma.

Now a method for the production of the novel vitamin E derivatives of the present invention represented by the above general formula (I) will be described.

α-Tocopherol 6-chloroformate represented by the formula (II):

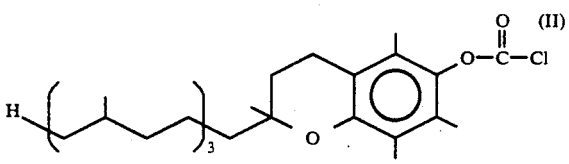

is condensed with either a polyhydric alcohol optionally protected with a protective group or an olefinic alcohol optionally protected with a protective group in the presence of a deacidifying agent such as pyridine, triethylamine, potassium carbonate or N,N′-dimethylaniline to thereby give a carbonate. The protective group is then removed in a conventional manner, if required. The obtained product is epoxidized with a peracid and then subjected to ring-opening reaction with perchloric acid to thereby give a polyhydroxyalkyl 2,5,7,8-tetramethyl-2-(4′,8′,12′-trimethyltridecyl)-6-chromanyl carbonate represented by the following general formula (III):

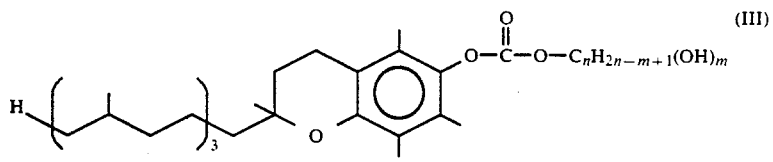

wherein m and n are as defined above.

Alternately, the compound of the above general formula (III) is obtained by reacting a polyhydric alcohol or an olefinic alcohol, each optionally protected with a protective group, with phosgene or trichloromethyl chloroformate in the presence of a deacidifying agent and then condensing the obtained product with α-tocopherol in the presence of a deacidifying agent.

Next, the compound of the general formula (III) is reacted with nicotinic acid or a reactive derivative thereof in a conventional manner to thereby give an ester. Thus a novel vitamin E derivative represented by the general formula (I) is obtained.

The polyhydric alcohol to be used in the present invention means an alcohol having two or more hydroxyl groups. The olefinic alcohol to be used in the present invention means an alcohol having unsaturated double bond(s).

Particular examples of the polyhydric alcohol, polyhydric alcohol protected with a protective group, olefinic alcohol and olefinic alcohol protected with a protective group include 1,3-bis(2-tetrahydro-pyranyloxy)-propan-2-ol, isopropylideneglycerol, 2-buten-1-ol, 2-methyl-2-propen-1-ol, 2,2-dimethyl-1,3-dioxolan-4-ylethanol, 1,4-bis(benzyloxy)-2,3-butanediol, 4-benzyloxy-2-buten-1-ol, 2,2-bis-(hydroxymethyl)propan-1-ol, 3-methyl-2-buten-1-ol, 4-(2-tetrahydropyranyloxy)-3-(2-tetrahydro-pyranyloxymethyl)butan-1-ol, 4-benzyloxy-2-hydroxy-2-methylbutan-1-ol, 3-methyl-3-buten-1-ol, monobenzal-pentaerythritol, 4-benzyloxy-2,3-epoxy-3-methylbutan-1-ol, 2,3,4,5-dibenzylidenexylitol, 5-ethyl-2,2-dimethyl-1,3-dioxan-5-ylmethanol and 4-hydroxy-3,3-bis(hydroxymethyl)butan-1-ol.

The process for the production of the novel vitamin E derivatives represented by the general formula (I) according to the present invention may be summarized as follows.

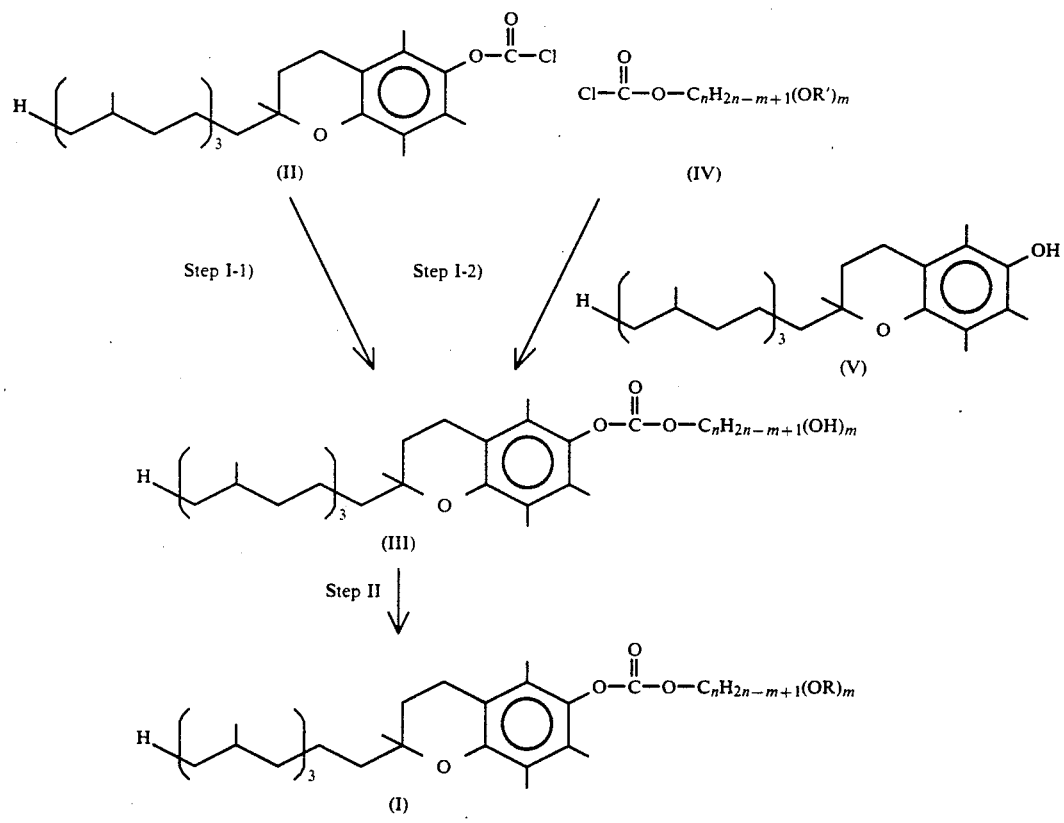

wherein R, m and n are as defined above; and R' represents a protective groups of a hydroxyl group. Now each step will be described in detail.

Step I

1) The hydroxide of the formula (III) is prepared from the starting α-tocopherol 6-chloroformate of the formula (II) by one of the following methods (1) to (3).

(1) The compound of the formula (II) is directly condensed with 1.5 to 4 equivalents of the corresponding polyhydric alcohol in the presence of a deacidifying agent such as pyridine, triethylamine or potassium carbonate to thereby give a hydroxide of the formula (III).

(2) The compound of the formula (II) is condensed with 1.0 to 1.5 equivalents of a polyhydric alcohol, wherein hydroxyl groups other than those located in the reactive site are protected with protective groups, in the presence of a deacidifying agent such as pyridine, triethylamine or N,N'-dimethylaniline. Then the protective groups in the carbonate thus obtained are removed with an inorganic acid such as hydrochloric acid in an organic solvent such as ethanol or methanol to thereby give a hydroxide represented by the formula (III). Examples of the protective group for protecting a hydroxyl group include isopropylideneketal, benzylideneacetal, benzyl ether, tetrahydropyranyl ether and methoxymethyl ether.

(3) The compound of the formula (II) is condensed with 1.0 to 1.5 equivalents of the corresponding olefinic alcohol in the presence of a deacidifying agent such as pyridine, triethylamine or N,N'-dimethylaniline. The carbonate thus obtained is then epoxidized with a peracid.

Examples of the peracid include peracetic acid, perbenzoic acid and m-chloroperbenzoic acid.

Next, the epoxide is subjected to ring-opening reaction with perchloric acid to thereby give a hydroxide represented by the formula (III).

2) One of the above-mentioned polyhydric alcohols and olefinic alcohols, wherein hydroxyl groups are protected with protective groups, is reacted with an equivalent amount of phosphogene or trichloromethyl chloroformate in the presence of a deacidifying agent such as pyridine, triethylamine or N,N'-dimethylaniline.

and subjected to ring-opening reaction by the same method as the one described in the above 1)–(3). Thus a hydroxide represented by the formula (III) is obtained.

Step II

1) The compound of the general formula (III) is reacted with 1.0 to 1.5 equivalents of nicotinoyl chloride hydrochloride, optionally in the presence of an aprotic polar solvent such as a halogenated hydrocarbon, an ether or a ketone, in the presence of a deacidifying agent such as a tertiary amine (for example, triethylamine, pyridine or N,N'-dimethylaniline) or potassium carbonate under ice-cooling or by heating under reflux. Thus the novel vitamin E derivative represented by the general formula (I) is obtained.

2) The compound of the general formula (III) is reacted with 1.0 to 1.5 equivalents of nicotinic acid in an aprotic polar solvent in the presence of a condensing agent such as 2-bromo-1-methylpyridinium iodide at room temperature or by heating under reflux. Thus the novel vitamin E derivative represented by the general formula (I) is obtained.

Particular examples of the vitamin E derivatives represented by the general formula (I) of the present invention are as follows.

2-Nicotinoyloxy-1-nicotinoyloxymethylethyl 2,5,7,8-tetramethyl-2-(4',8',12'-trimethyltridecyl)-6-chromanyl carbonate [Compound 1].

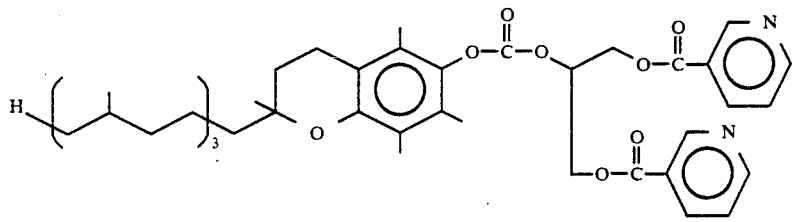

The chloroformate (IV) thus obtained is then condensed with an equivalent amount of α-tocopherol (V) in the presence of a deacidifying agent such as pyridine, 2,3-Bis(nicotinoyloxy)propyl 2,5,7,8-tetramethyl-2-(4',8',12'-trimethyltridecyl)-6-chromanyl carbonate [Compound 2].

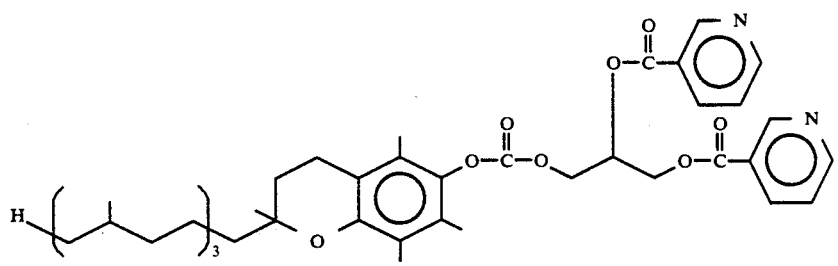

triethylamine or N,N'-dimethylaniline. From the carbonate thus obtained, the protective groups are removed by the same method as the one described in the above 1)–(2). Alternately, the carbonate is epoxidized 2,3-Bis(nicotinoyloxy)butyl 2,5,7,8-tetramethyl-2-(4',8',12'-trimethyltridecyl)-6-chromanyl carbonate [Compound 3].

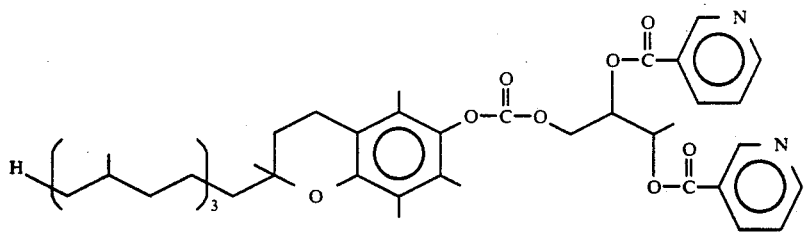

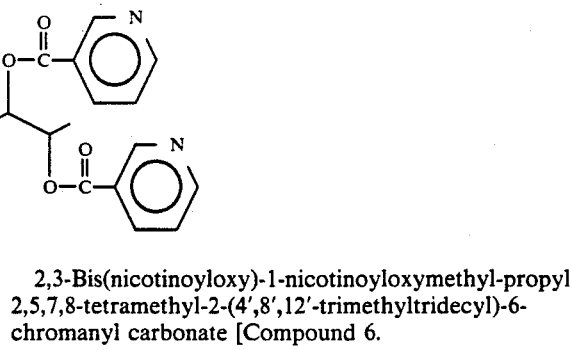

2-Methyl-2,3-bis(nicotinoyloxy)propyl 2,5,7,8-tetramethyl-2-(4',8',12'-trimethyltridecyl)-6-chromanyl carbonate [Compound 4].

2,3-Bis(nicotinoyloxy)-1-nicotinoyloxymethyl-propyl 2,5,7,8-tetramethyl-2-(4',8',12'-trimethyltridecyl)-6-chromanyl carbonate [Compound 6].

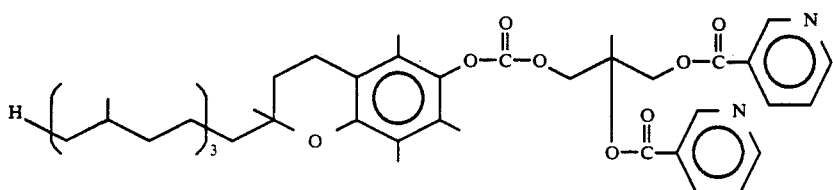

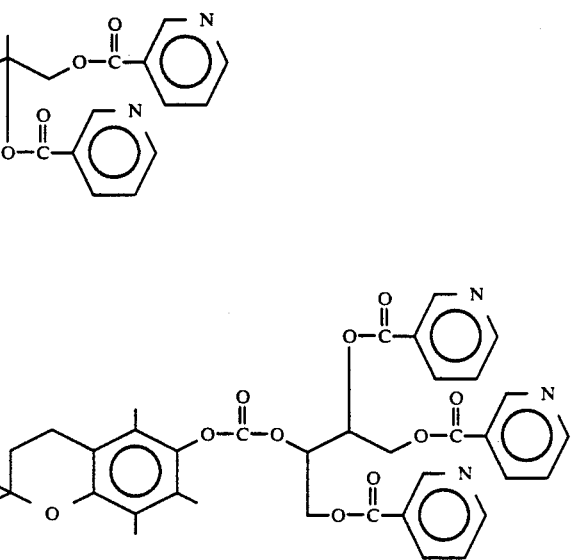

3,4-Bis(nicotinoyloxy)butyl 2,5,7,8-tetramethyl-2-(4',8',12'-trimethyltridecyl)-6-chromanyl carbonate [Compound 5].

2,3,4-Tris(nicotinoyloxy)butyl 2,5,7,8-tetramethyl-2-(4',8',12'-trimethyltridecyl)-6-chromanyl carbonate [Compound 7].

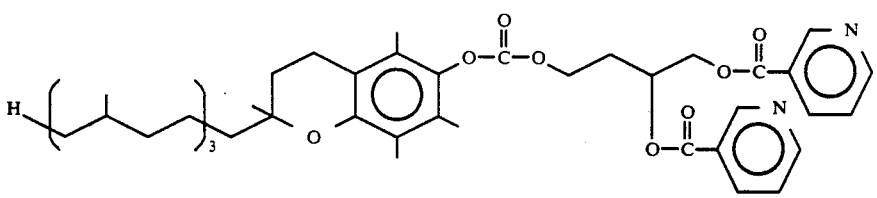

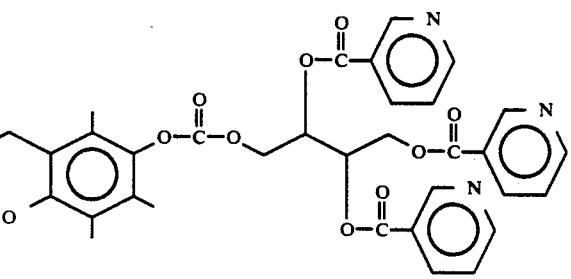

2,2-Bis(nicotinoyloxymethyl)propyl 2,5,7,8-tetramethyl-2-(4',8',12'-trimethyltridecyl)-6-chromanyl carbonate [Compound 8].

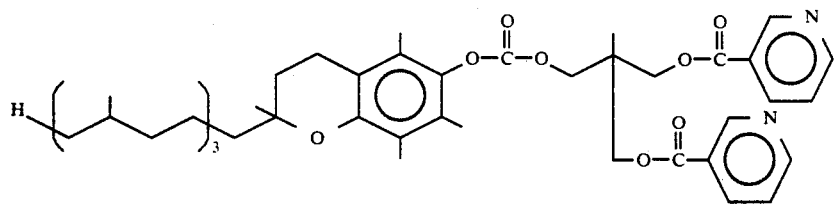

3-Methyl-2,3-bis(nicotinoyloxy)butyl 2,5,7,8-tetramethyl-2-(4′,8′,12′-trimethyltridecyl)-6-chromanyl carbonate [Compound 9].

2-Methyl-2,4-bis(nicotinoyloxy)butyl 2,5,7,8-tetramethyl-2-(4′,8′,12′-trimethyltridecyl)-6-chromanyl carbonate [Compound 11].

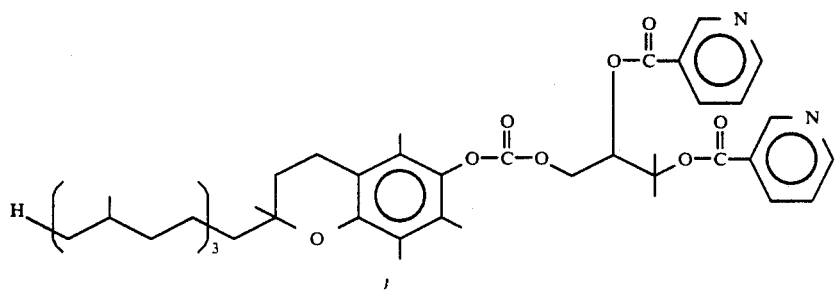

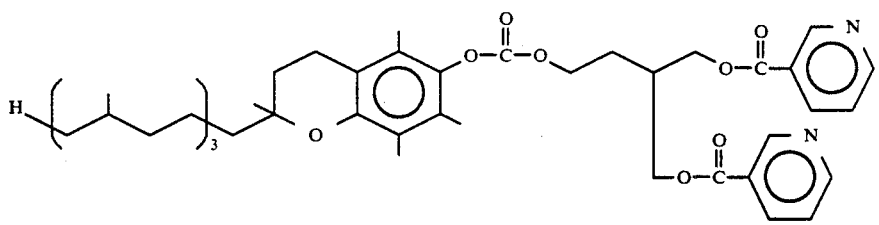

4-Nicotinoyloxy-3-nicotinoyloxymethylbutyl 2,5,7,8-tetramethyl-2-(4′,8′,12′-trimethyltridecyl)-6-chromanyl carbonate [Compound 10].

3-Methyl-3,4-bis(nicotinoyloxy)butyl 2,5,7,8-tetramethyl-2-(4′,8′,12′-trimethyltridecyl)-6-chromanyl carbonate [Compound 12].

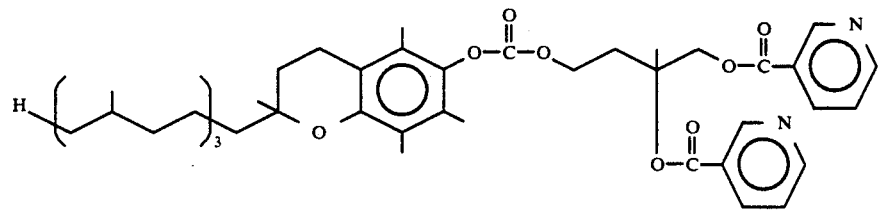

3-Nicotinoyloxy-2,2-bis(nicotinoyloxymethyl)-propyl 2,5,7,8-tetramethyl-2-(4′,8′,12′-trimethyltridecyl)-6-chromanyl carbonate [Compound 13].

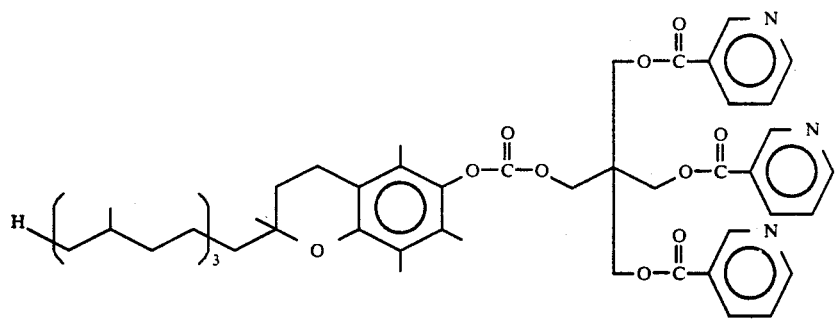

2-Methyl-2,3,4-tris(nicotinoyloxy)butyl 2,5,7,8-tetramethyl-2-(4′,8′,12′-trimethyltridecyl)-6-chromanyl carbonate [Compound 14].

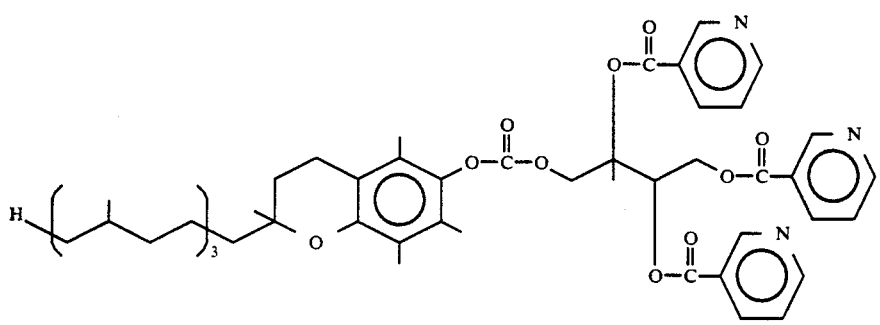

3-Methyl-2,3,4-tris(nicotinoyloxy)butyl 2,5,7,8-tetramethyl-2-(4′,8′,12′-trimethyltridecyl)-6-chromanyl carbonate [Compound 15].

2,3,4,5-Tetrakis(nicotinoyloxy)pentyl 2,5,7,8-tetramethyl-2-(4′,8′,12′-trimethyltridecyl)-6-chromanyl carbonate [Compound 16].

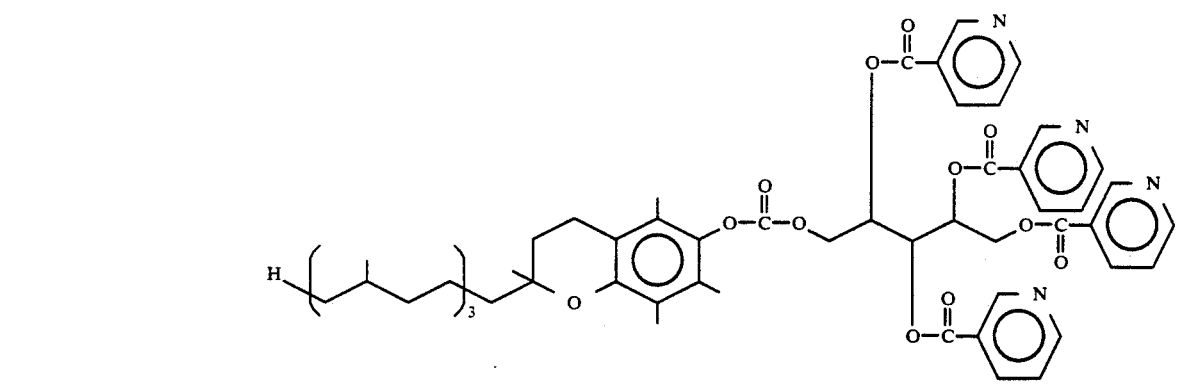

2,2-Bis(nicotinoyloxy)butyl 2,5,7,8-tetramethyl-2-(4′,8′,12′-trimethyltridecyl)-6-chromanyl carbonate [Compound 17].

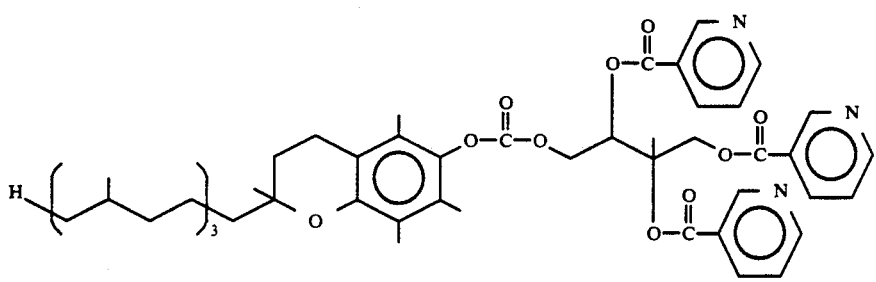

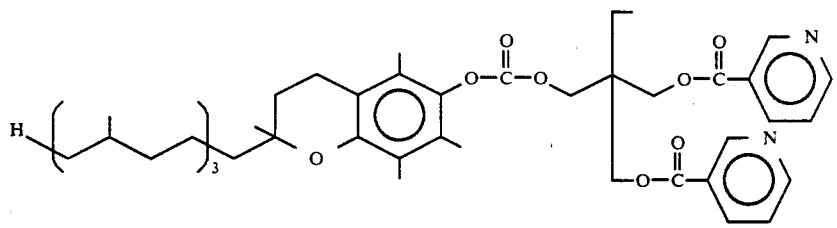

4-Nicotinoyloxy-3,3-bis(nicotinoyloxy)butyl 2,5,7,8-tetramethyl-2-(4′,8′,12′-trimethyl-tridecyl)-6-chromanyl carbonate [Compound 18].

e: Nicotinic acid

FIG. 2

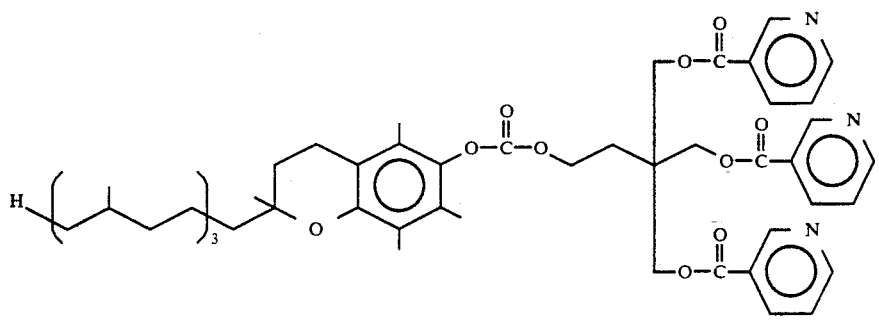

BRIEF DESCRIPTION OF THE DRAWINGS

FIG. 1
a: Plasma nicotinic acid level (μg/ml)
b: Time
c: Invention compound (2)
d: Invention compound (5)

Figure 1:
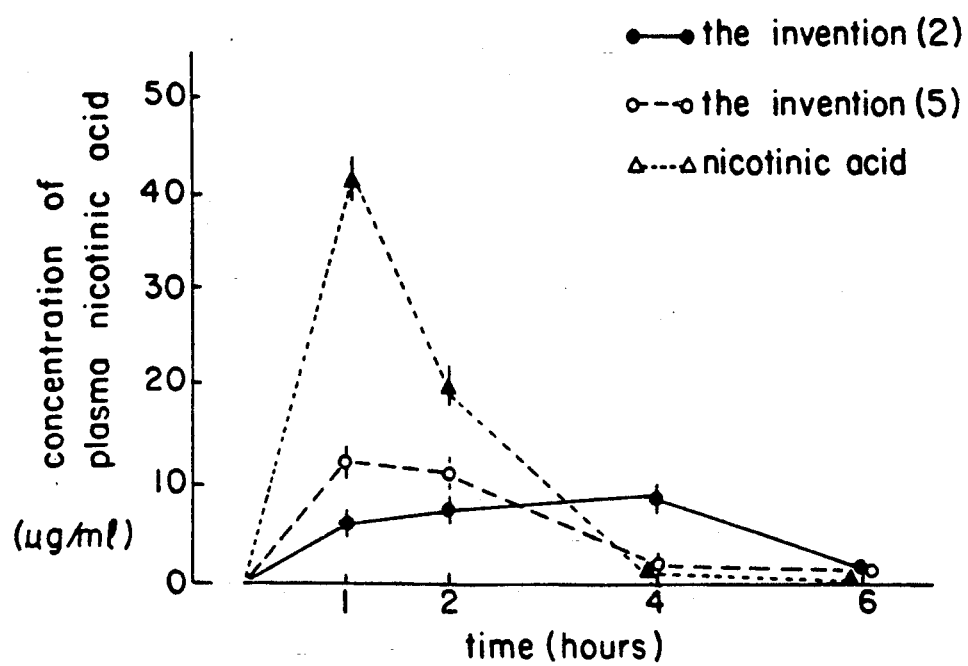
FIG. 1 shows changes in plasma nicotinic acid levels of rats to which he invention compounds (2) and (5) and nicotinic acid were given.

a: Plasma vitamin E level (μg/ml)
b: Time
c: Invention compound (2)
d: Cottonseed oil alone

EXAMPLES

To further illustrate the present invention, and not by way of limitation, the following Examples will be given.

EXAMPLE 1

2-Nicotinoyloxy-1-nicotinoyloxymethylethyl 2,5,7,8-tetramethyl-b
2-(4′,8′,12′-trimethyltridecyl)-6-chromanyl carbonate [Compound 1]

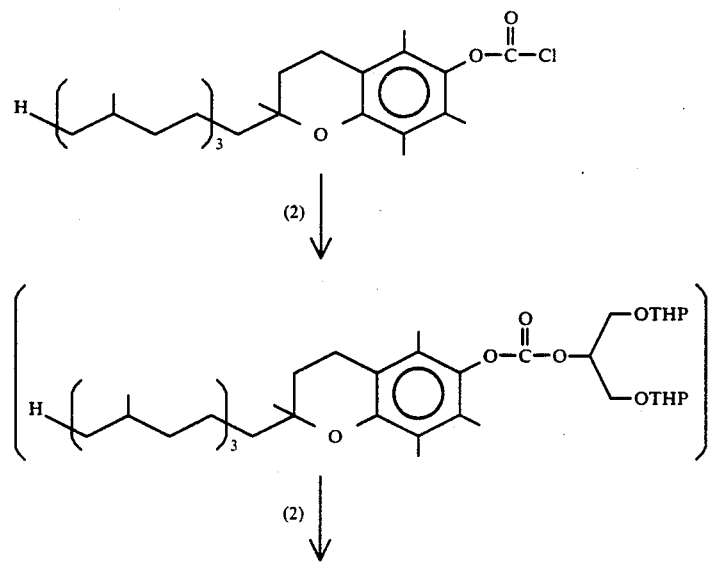

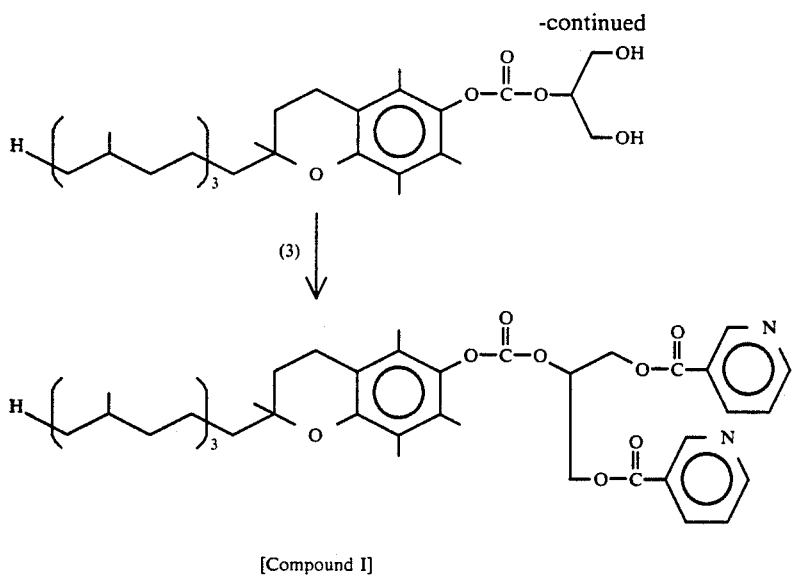

[Compound I]

(1) Synthesis of 1,3-bis(2-tetrahydropyranyloxy)-propan-2-ol 9.0 g of dihydroxyacetone dimer, 21.0 g of 3,4-dihydro-2H-pyran and a catalytic amount of p-toluenesulfonic acid were added to 70 ml of dichloromethane and stirred under ice-cooling for 3 hours. After the completion of the reaction, 150 ml of diethyl ether was added thereto. The mixture was then washed with a saturated aqueous solution of sodium hydrogencarbonate and dried over anhydrous magnesium sulfate. After distilling off the solvent, the oily residue thus obtained was subjected to chromatography wherein silica gel was employed as a carrier while hexane/ethyl acetate was employed as a mobile phase. Thus 16.5 g of 1,3-bis(2-tetrahydro-pyranyloxy)propan-2-one was obtained as a colorless viscous liquid.

5.4 g (0.02 mol) of the obtained compound was then dissolved in a mixture of 50 ml of tetrahydrofuran with 3 ml of water and cooled to 5° C. After adding 0.4 g (0.01 mmol) of sodium borohydride thereto, the mixture was stirred at the same temperature for 1 hour. 0.4 g (0.01 mol) of sodium borohydride was further added thereto and the stirring was continued for additional 1 hour. After decomposing the excessive sodium borohydride, the reaction mixture was extracted with ethyl acetate. The extract was washed with water and dried over anhydrous magnesium sulfate. After distilling off the solvent, the obtained oily residue was subjected to chromatography wherein silica gel was used as a carrier while hexane/ethyl acetate was used as a mobile phase. Thus 4.2 g of 1,3-bis(2-tetrahydropyranyloxy)propan-2-ol was obtained as a colorless viscous liquid.

(2) Synthesis of 2-hydroxy-1-hydroxymethylethyl 2,5,7,8-tetramethyl-2-(4',8',12'-trimethyl-tridecyl)-6-chromanyl carbonate To a mixture comprising 2.8 g (0.01 mol) of 1,3-bis(2-tetrahydropyranyloxy)propan-2-ol, 7.7 ml of pyridine and 25 ml of dichloromethane was added dropwise a solution of 5.5 g (0.011 mol) of α-tocopherol 6-chloroformate in 20 ml of dichloromethane under stirring within 20 minutes. Further, the stirring was continued for 15 hours at room temperature. Next, the reaction mixture was dissolved in 200 ml of ethyl acetate, washed with water and dried over anhydrous magnesium sulfate. After distilling off the solvent, the obtained oily residue was dissolved in 100 ml of methanol. Then 1.2 g of p-toluenesulfonic acid was added thereto and the mixture was stirred at room temperature for 40 minutes. The reaction mixture was poured into water and the oily material thus separated out was extracted with diethyl ether (hereinafter referred to simply as "ether"), washed with water and dried over magnesium sulfate. After distilling off the solvent, the obtained residue was purified by column chromatography (silica gel, hexane : ethyl acetate=7:3) to thereby give 4.8 g of the title compound as a colorless viscous liquid.

$^1$H-NMR spectrum: (60 MHz, CDCl$_3$) δ; 0.60–1.90 (m, 38H), 1.9–2.15 (m, 9), 2.55 (t, 2H), 3.00 (s, 2H, disappeared by adding D$_2$O), 3.80 (d, 4H), 4.6–4.9 (m, 1H).

(3) Synthesis of 2-nicotinoyloxy-1-nicotinoyloxy-methylethyl 2,5,7,8-tetramethyl-2-(4',8',12'-trimethyltridecyl)-6-chromanyl carbonate To a suspension comprising 3.7 g (0.007 mol) of 2-hydroxy-1-hydroxymethylethyl 2,5,7,8-tetramethyl-2-(4',8',12'-trimethyltridecyl)-6-chromanyl carbonate, 3.6 g (0.021 mol) of nicotinoyl chloride hydrochloride and 50 ml of dichloromethane was added dropwise 5.4 g of triethylamine under ice-cooling and stirring. After stirring at room temperature for 14 hours, the reaction mixture was poured into water, extracted with ether, washed with water and dried over magnesium sulfate. After distilling off the solvent, the obtained crude product was purified by column chromatography (silica gel, chloroform). Thus 3.8 g of the title compound [compound 1]was obtained as a pale yellow, transparent and viscous liquid.

$^1$H-NMR spectrum (60 MHz, CDCl$_3$) δ; 0.60 ~1.80(m, 38H), 1.92, 1.95, 2.00 (s×3, 9H), 2.55(t,2H), 4.7~4.85 (m,4H), 5.55(m,1H), 7.40(m,2H), 8.3 (m,2H), 8.8(m,2H), 9.25(m,2H)

EXAMPLE 2

2,3-Bis(nicotinoyloxy)propyl 2,5,7,8-tetramethyl-2-(4',8',12'-trimethyltridecyl)-6-chromanyl carbonate [Compound 2]

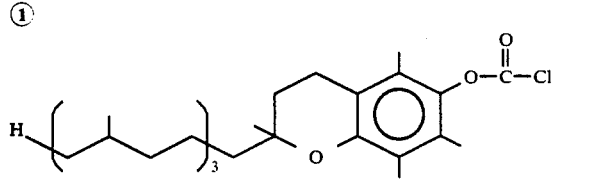

(1) ↓

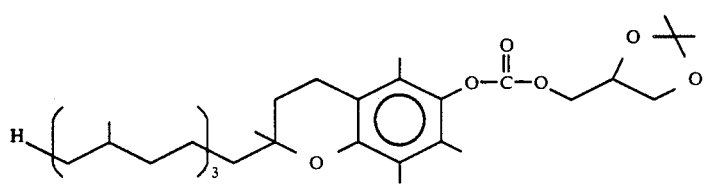

(2) ↓

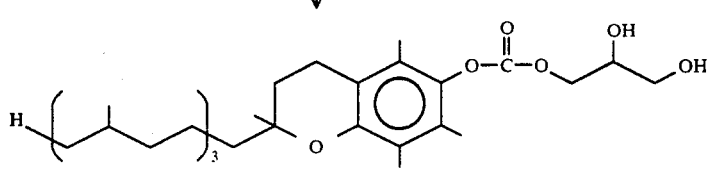

(3) ↓

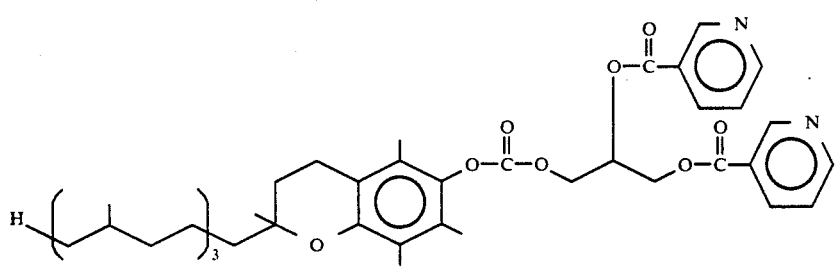

[Compound 2]

(1) Synthesis of 2,2-dimethyl-1,3-dioxolan-4-ylmethyl 2,5,7,8-tetramethyl-2-(4',8',12'-trimethyl-tridecyl)-6-chromanyl carbonate To a mixture comprising 1.8 g (0.012 mol) of isopropylideneglycerol, 1.2 g (0.015 mol) of pyridine and 50 ml of dichloromethane was slowly added a solution of 5.0 g (0.01 mol) of α-tocopherol 6-chloroformate in 20 ml of dichloromethane under ice-cooling and stirring. After stirring at room temperature for 2 hours, the reaction mixture was poured into water, extracted with ether, successively washed with diluted hydrochloric acid, water, an aqueous solution of sodium hydrogencarbonate and water, and dried over magnesium sulfate. After distilling off the solvent, the obtained oily residue was purified by column chromatography (silica gel, benzene) to thereby give 5.6 g of the title compound as a pale yellow, transparent and viscous liquid.

(2) Synthesis of 2,3-dihydroxypropyl 2,5,7,8-tetramethyl-2-(4',8',12'-trimethyltridecyl)-6-chromanyl carbonate A mixture comprising 3.9 g of 2,2-dimethyl-1,3-dioxolan-4-ylmethyl 2,5,7,8-tetramethyl-2-(4',8',12'-trimethyltridecyl)-6-chromanyl carbonate, 15 ml of tetrahydrofuran, 5 ml of methanol and 5 ml of 2 N hydrochloric acid was stirred and heated under reflux for 3 hours. The reaction mixture was dissolved in ether, successively washed with water, an aqueous solution of sodium hydrogencarbonate and water, and dried over magnesium sulfate. After distilling off the solvent, the obtained oily residue was purified by column chromatography (silica gel, hexane : ethyl acetate=3.5:1.5) to thereby give 3.3 g of the title compound as a pale yellow, viscous liquid.

$^1$H-NMR spectrum (60 MHz, CDCl$_3$) δ: 0.60–1.90 (m, 38H), 1.9–2.15 (m, 9H), 2.55 (t, 2H), 3.2 (s, 2H, disappeared by adding D₂O) 3.5-4.0 (m, 3H), 4.2 (d, 2H).

IR (cm⁻¹ Nujol): 1760 (O-CO-O), 3400 (OH).

(3) Synthesis of 2,3-bis(nicotinoyloxy)propyl 2.5,7,8-tetramethyl-2-(4',8',12'-trimethyl-tridecyl)-6-chromanyl carbonate To a suspension comprising 5.5 g (0.01 mol) of 2,3-dihydroxypropyl 2,5,7,8-tetramethyl-2-(4',8',12'-trimethyltridecyl)-6-chromanyl carbonate, 5.4 g (0.03 mol) of nicotinoyl chloride hydrochloride and 100 ml of dry dichloromethane was slowly added dropwise 6.4 g (0.063 mol) of triethylamine under ice-cooling. After the completion of the addition, the reaction mixture was stirred at room temperature for 2 hours and then poured into ice/water. The reaction product was extracted with chloroform, repeatedly washed with water and dried over magnesium sulfate. After distilling off the solvent, the obtained oily crude product was purified by column chromatography (silica gel, benzene: ethyl acetate=4:1) to thereby give 5.7 g of the title compound [compound 2] as a pale yellow, transparent and viscous liquid.

¹H-NMR spectrum (60 MHz, CDCl₃) δ; 0.70~1.80(m,38H), 1.93, 1.97, 2.05 (s×3, 9H), 2.50(t,2H), 4.6~4.85 (m,4H), 5.8(m,1H), 7.40(m,2H), 8.3 (m,2H), 8.8(m,2H), 9.2(m,2H)

IR (cm⁻¹ Nujol) ; 1760, 1730 (O-CO-O, COOAr)

(4) Another method of synthesis of 2 3-dihydroxypropyl 2,5,7,8-tetramethyl-2-(4',8',12'-trimethyltridecyl)-6-chromanyl carbonate To a mixture comprising 11.1 g (0.12 mol) of glycerol, 38 ml of pyridine and 20 ml of dichloromethane was slowly added dropwise 19.7 g (0.04 mol) of α-tocopherol 6-chloroformate within 30 minutes under stirring at −10° C. After the completion of the addition, the mixture was stirred overnight at room temperature. Then it was diluted with ethyl acetate, successively washed with water, diluted hydrochloric acid and water, and dried over magnesium sulfate. After distilling off the solvent, the obtained oily crude product was purified by column chromatography (silica gel, hexane : ethyl acetate =3.5 : 1.5) to thereby give 19.2 g a pale yellow, transparent and viscous liquid which was identified with 2,3-dihydroxypropyl 2,5,7,8-tetramethyl-2-(4',8',12'-trimethyltridecyl)-6-chromanyl carbonate obtained in (2). This product possessed a purity comparable to the one obtained in (2).

(5) Another method of synthesis of 2,2-dimethyl-1,3-dioxolan-4-ylmethyl 2,5,7,8-tetramethyl-2-(4',8',12'-trimethyltridecyl)-6-chromanyl carbonate To a mixture comprising 6.6 g (0.05 mol) of isopropylideneglycerol, 5.9 g (0.03 mol) of trichloromethyl chloroformate and 50 ml of toluene was slowly added dropwise 7.3 g (0.06 mol) of N,N-dimethylaniline dissolved in 20 ml of toluene. After stirring at room temperature for 4 hours, the reaction mixture was poured into diluted hydrochloric acid, extracted with ethyl acetate, washed with water, and dried over magnesium sulfate. After distilling off the solvent, 10.4 g of 2,2-dimethyl-1,3-dioxolan-4-ylmethyl chloroformate was obtained as a colorless liquid. This product showed a single spot in thin layer chromatography (silica gel, benzene: ethyl acetate=10:3) and was satisfactory in NMR data [(60 MHz, CDCl₃) α; 1.25, 1.30 (s×2, 6H), 3.1-3.7 (m, 4H), 3.8-4.1 (m, 2H), 3.6 (s, 1H, disappeared by adding D₂O)]. Thus it was not purified but directly used in the subsequent step.

To a mixture comprising 2.2 g (0.005 mol) of α-tocopherol, 1.4 g (0.007 mol) of 2,2-dimethyl-1,3-dioxolan-4-ylmethyl chloroformate and 30 ml of dichloromethane was slowly added dropwise 0.8 g of pyridine dissolved in 10 ml of dichloromethane under ice-cooling. After stirring at room temperature overnight, the reaction mixture was poured into diluted hydrochloric acid, extracted with ethyl acetate, washed with water, and dried over magnesium sulfate. After distilling off the solvent, the obtained residue in the form of a yellow, oily and viscous liquid was purified by column chromatography (silica gel, benzene) to thereby give 2.7 g of a pale yellow, viscous liquid which was identified with 2,2,-dimethyl-1,3-dioxolan-4-ylmethyl 2,5,7,8-tetramethyl-2-(4',8',12'-trimethyltridecyl)-6-chromanyl carbonate obtained in (1). This compound possessed a purity comparable to the one obtained in (1).

EXAMPLE 3

2,3-Bis(nicotinoyloxy)butyl 2,5,7,8-tetramethyl-2-(4',8',12'-trimethyltridecyl)-6-chromanyl carbonate [Compound 3]

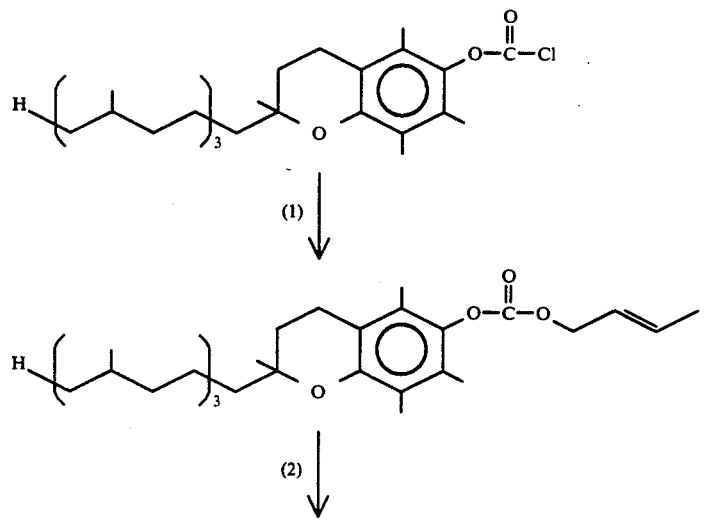

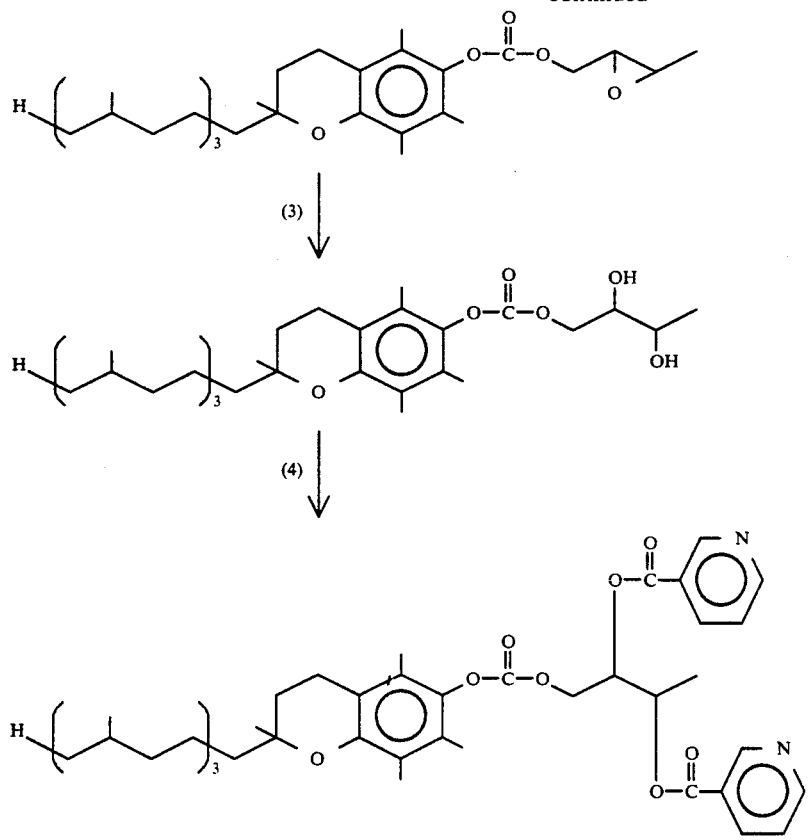

[Compound 3]

(1) Synthesis of 2-butenyl 2,5,7,8-tetramethyl-2-(4',8',12'-trimethyltridecyl)-6-chromanyl carbonate To a mixture comprising 19.7 g (0.04 mol) of α-tocopherol 6-chloroformate, 5.8 g (0.08 mol) of 2-buten-1-ol and 100 ml of dichloromethane was added dropwise 6.3 g of pyridine under ice-cooling and stirring. The stirring was further continued for 30 minutes. Then the reaction mixture was successively washed with diluted hydrochloric acid and water, and dried. After distilling off the solvent, the obtained oily residue was purified by column chromatography (silica gel, hexane : ethyl acetate=100:2) to thereby give 18.0 g of the title compound as a colorless viscous liquid.

(2) Synthesis of 2,3-epoxybutyl 2,5,7,8-tetramethyl-2-(4',8',12'-trimethyltridecyl)-6-chromanyl carbonate A solution of 18.0 g (0.034 mol) of 2-butenyl 2,5,7,8-tetramethyl-2-(4',8',12'-trimethyltridecy)-6-chromanyl carbonate in 100 ml of dichloromethane was added dropwise to another solution of 8.4 g (0.034 mol) of m-chloroperbenzoic acid (purity: 70%) in 200 ml of dichloromethane under ice-cooling and stirring within 45 minutes. After stirring at 0° to 5° C. for 2 hours, the reaction mixture was further stirred at room temperature for 2 days. Then the reaction mixture was extracted by adding 20 ml of a 20% aqueous solution of sodium hydrosulfite. The extract was washed with a 1% aqueous solution of sodium hydrogencarbonate twice and then with water twice, and dried over magnesium sulfate. After distilling off the solvent, the obtained oily residue was purified by column chromatography (silica gel, hexane : ethyl acetate=100:4) to thereby give 4.7 g of the 695 title compound as a colorless viscous liquid.

(3) Synthesis of 2,3-dihydroxybutyl 2,5,7,8-tetramethyl-2-(4',8',12'-trimethyltridecyl)-6-chromanyl carbonate 4.5 g of 2,3-epoxybutyl 2,5,7,8-tetramethyl-2-(4',8',12'-trimethyltridecyl)-6-chromanyl carbonate was dissolved in 200 ml of tetrahydrofuran and 10 ml of 20% perchloric acid was added thereto. The resulting mixture was stirred at room temperature for 24 hours. Then the reaction mixture was extracted with 500 ml of ethyl acetate, washed with 300-ml portions of water thrice, and dried over magnesium sulfate. After distilling off the solvent, the obtained residue was purified by column chromatography (silica gel, benzene : ethyl acetate=100:15) to thereby give 1.8 g of the title compound as a colorless viscous liquid.

(4) Synthesis of 2,3-bis(nicotinoyloxy)butyl 2,5,7,8-tetramethyl-2-(4',8',12'-trimethyltridecyl)-6-chromanyl carbonate 1.5 g (0.0027 mol) of 2,3-dihydroxybutyl 2,5,7,8-tetramethyl-2-(4',8',12'-trimethyltridecyl)-6-chromanyl carbonate and 1.6 g (0.009 mol) of nicotinoyl chloride hydrochloride were added to 100 ml of dry dichloromethane, and 3 ml of pyridine was slowly added dropwise thereto while stirring at −20° C. After the completion of the addition, the resulting mixture was stirred at the same temperature for 2 hours and then poured into water. The organic phase was collected, washed with water and dried. After distilling off the solvent, the obtained oily residue was purified by column chromatography (silica gel, benzene : ethyl acetate=5:1) to thereby give 1.8 g of the title compound [compound 3].

$^1$H-NMR spectrum (60MHz, CDCl$_3$)δ; 0.8~1.9(m,41H), 1.92, 1.96, 2.04 (s×3,9H), 2.50(t,2H), 4.65(d,2H), 5.60(m,1H), 5.70(m,1H), 7.40(m,2H), 8.30(m,2H), 8.78(m,2H), 9.20(m,2H)
IR (cm$^{-1}$ Nujol) ; 1760, 1730 (O-CO-O, COOAr)

EXAMPLE 4

2-Methyl-2,3-bis(nicotinoyloxy)propyl 2,5,7,8-tetramethyl-2-(4',8',12'-trimethyltridecyl)-6-chromanyl carbonate [Compound 4]

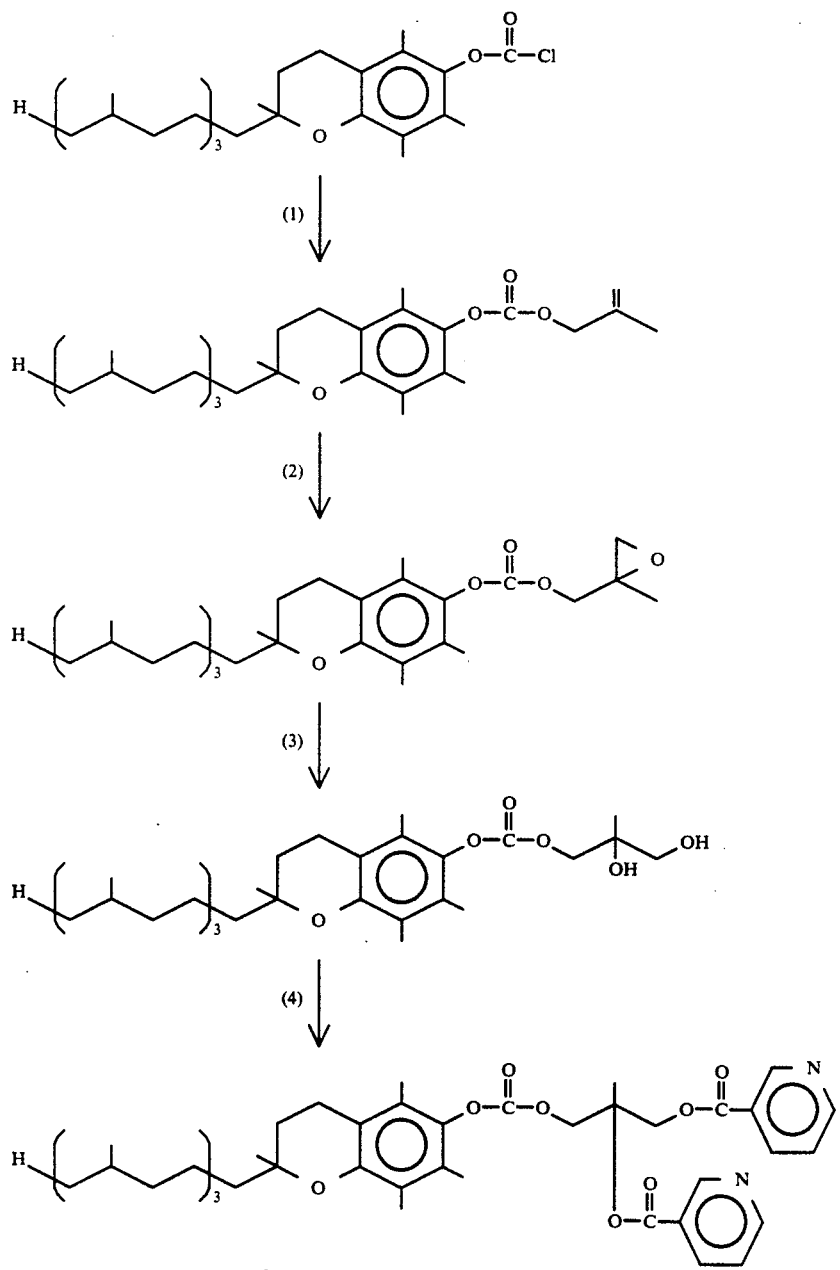

[Compound 4]

(1) Synthesis of 2-methyl-2-propenyl 2,5,7,8-tetramethyl-2-(4',8',12'-trimethyltridecyl)-6-chromanyl carbonate To a solution of 2.0 g (0.027 mol) of 2-methyl-propen-1-ol in 30 ml of pyridine was slowly added dropwise 30 ml of a solution of 10.0 g (0.02 mol) of α-tocopherol 6-chloroformate in ether under ice-cooling and stirring. After the completion of the addition, the reaction mixture was further stirred for 2 hours and then acidified by pouring into diluted hydrochloric acid. Then it was extracted with ether and the extract was washed with water and dried over magnesium sulfate. After distilling off the solvent, the obtained oily yellow residue was purified by column chromatography (silica gel, hexane : benzene = 2:1) to thereby give 9.5 g of the title compound as a colorless oily matter.

(2) Synthesis of 2,3-epoxy-2-methylpropyl 2,5,7,8-tetramethyl-2-(4',8',12'-trimethyltridecyl)-6-chromanyl carbonate To a solution of 9.0 g (0.017 mol) of 2-methyl-2-trimethyltridecyl)-6-chromanyl carbonate in 100 ml of dichloromethane was added 5.9 g (0.024 mol) of m-chloroperbenzoic acid (purity: 70%) in four portions under ice-cooling and stirring. The resulting mixture was stirred at 5° C. for 1 hour. After filtering off the white precipitate thus formed, 20 ml of a 20% aqueous solution of sodium hydrosulfite was added to the reaction mixture. The mixture was extracted with dichloromethane and the extract was successively washed with an aqueous solution of sodium hydrogencarbonate and water, and dried over magnesium sulfate. After distilling off the solvent, the obtained oily residue was purified by column chromatography (silica gel, hexane : ethyl acetate = 100:4) to thereby give 6.6 g of the title compound as a colorless viscous liquid.

$^1$H-NMR spectrum (60MHz, CDCl$_3$) δ; 0.7~1.6(m,36H), 1.42(s,3H), 1.75 (m,2H), 1.92, 1.96, 2.04(s×3,9H), 2.45(t,2H0, 2.60(dd,2H), 4.20(d,2H)

(3) Synthesis of 2,3-dihydroxy-2-methylpropyl 2,5,7,8-tetramethyl-2-(4',8',12'-trimethyltridecyl)-6-chromanyl trimethyltridecyl)-6-chromanyl carbonate To a mixture comprising 4.3 g (0.0079 mol) of 2,3-epoxy-2-methylpropyl 2,5,7,8-tetramethyl--(4',8',12'-trimethyltridecyl)-6-chromanyl carbonate, 150 ml of tetrahydrofuran and 50 ml of water was added dropwise 10 ml of 60% perchloric acid dissolved in 20 ml of water under ice-cooling and stirring. After the completion of the addition, the mixture was further stirred for additional 4 hours and then poured into ice/water. After confirming that no peroxide was contained therein with potassium iodide starch paper, the mixture was extracted with ether. The extract was then washed with water and dried. After distilling off the solvent, the obtained oily residue was purified by column chromatography (silica gel, benzene : ethyl acetate = 100:15) to thereby give 3.4 g of the title compound as a colorless viscous liquid.

$^1$H-NMR spectrum (60MHz, CDCl$_3$) δ; 0.7~1.6(m,39H), 1.80(m,2H), 2.0 (s,3H), 2.1(s,6H), 2.45(t,2H), 2.70(s,2H), 3.4~3.5(broad s,2H), 4.30(s,2H)

(4) Synthesis of 2-methyl-2,3-bis(nitocinoyloxy)-propyl 2,5,7,8-tetramethyl-2-(4',8',12'-trimethyltridecyl)-6-chromanyl carbonate 2.0 g (0.0035 mol) of 2,3-dihydroxy-2-methylpropyl 2,5,7,8-tetramethyl-2-(4',8', 12'-trimethyltridecyl)-6-chromanyl carbonate and 3 g of triethylamine were dissolved in 50 ml of dichloromethane. To the obtained solution was added 1.9 g (0.01 mol) of nicotinoyl chloride hydrochloride in three portions under ice-cooling. The resulting mixture was further stirred at the same temperature for 2 hours and poured into water. The organic phase was collected, washed with water and dried. After distilling off the solvent, the obtained oily residue was purified by column chromatography (silica gel, benzene : ethyl acetate = 5:1) to thereby give 1.5 g of the title compound [compound 4]as a colorless viscous liquid.

$^1$H-NMR spectrum (60MHz, CDCl$_3$) δ; 0.7~1.6(m,39H), 1.80(m,2H), 1.95, 2.00, 2.05(s×3,9H), 2.45(t,2H), 4.7~4.8(broad,4H), 7.20(m,2H), 8.10(m,2H), 8.55(m,2H), 9.10(m,2H)

IR (cm$^{-1}$ Nujol) ; 1765, 1730 (O—CO—O, COOAr)

EXAMPLE 5

Synthesis of 3,4-bis(nicotinoyloxy)butyl 2,5,7,8-tetramethyl-2-(4',8',12'-trimethyltridecyl)-6-chromanyl carbonate [Compound 5]

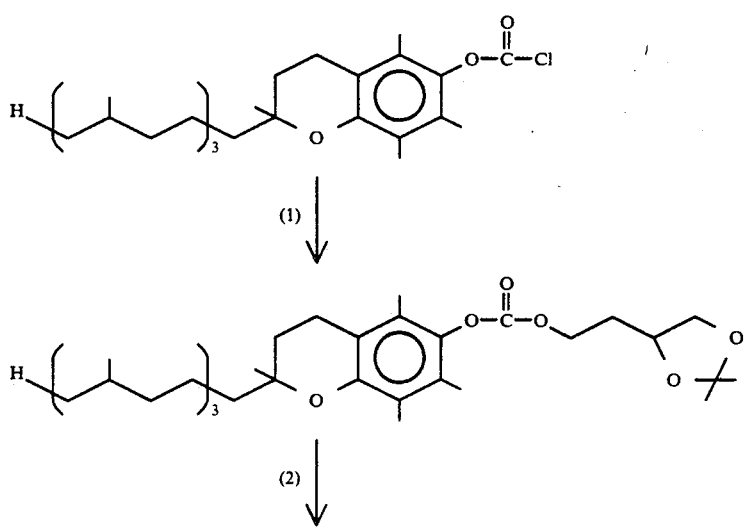

-continued

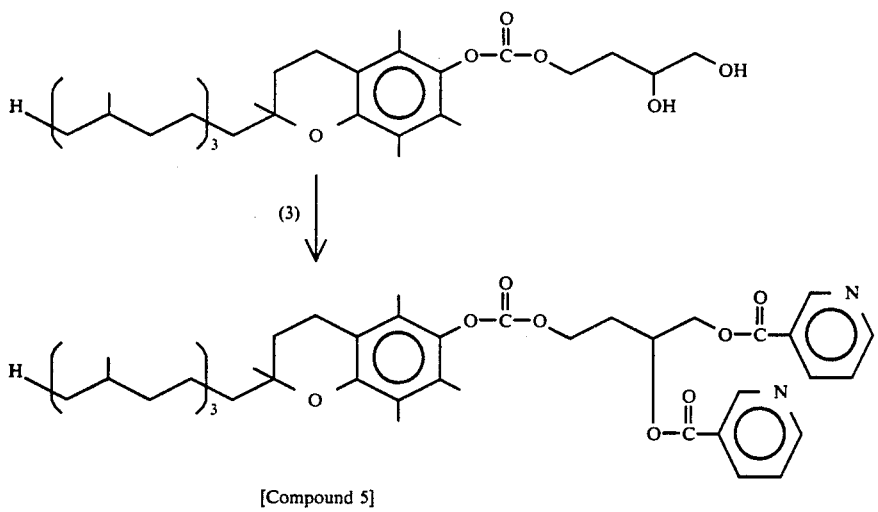

[Compound 5]

(1) Synthesis of 2,2-dimethyl-1,3-dioxolan-4-ylethyl 2,5,7,8-tetramethyl-2-(4',8',12'-trimethyl-tridecyl)-6-chromanyl carbonate To a mixture comprising 1.5 g (0.01 mol) of 2,2-dimethyl-1,3-dioxolan-4-ylethanol, 1.2 g (0.015 mol) of pyridine and 50 ml of dichloromethane was slowly added dropwise a solution of 5.0 g (0.01 mol) of α-tocopherol 6-chloroformate in 20 ml of dichloromethane under ice-cooling and stirring. Then the resulting mixture was stirred at room temperature for 2 hours. The reaction mixture was poured into water, extracted with ether, successively washed with diluted hydrochloric acid, water, an aqueous solution of sodium hydrogencarbonate and water, and dried. After distilling off the solvent, the obtained oily residue was purified by column chromatography (silica gel, benzene) to thereby give 5.2 g of the title compound as a pale yellow, transparent and viscous liquid.

(2) Synthesis of 3,4-dihydroxybutyl 2,5,7,8-tetramethyl-2-(4',8',12'-trimethyltridecyl)-6-chromanyl carbonate A mixture comprising 5.0 g of 2,2-dimethyl-1,3-dioxolan-4-yiethyl 2,5,7,8-tetramethyl-2-(4',8',12'-trimethyl-tridecyl)-6-chromanyl carbonate, 20 ml of tetrahydrofuran, 10 ml of methanol and 8 ml of 2N hydrochloric acid was heated under reflux for 3 hours with stirring. Then the reaction mixture was dissolved in ether, successively washed with water, an aqueous solution of sodium hydrogencarbonate and water, and dried. After distilling off the solvent, the obtained oily residue was purified by column chromatography (silica gel, hexane : ethyl acetate=3.5:1.5) to thereby give 4.2 g of the title compound as a pale yellow, viscous liquid.

$^1$H-NMR spectrum (60MHz, CDCl$_3$) δ; 0.70~1.90(m,4H), 1.95(s,3H), 2.00 (s,6H), 2.55(t,2H), 3.2~4.5(m,7H, 2H, among them disappeared by adding D$_2$O).

(3) Synthesis of 3,4-bis(nicotinoyloxy)butyl 2,5,7,8-tetramethyl-2-(4',8',12'-trimethyl-tridecyl)-6-chromanyl carbonate (i) To a suspension comprising 5.6 g (0.01 mol) of 3,4-dihydroxybutyl 2,5,7,8-tetramethyl-2-(4',8',12'-trimethyltridecyl)-6-chromanyl carbonate, 5.4 g (0.03 mol) of nicotinoyl chloride hydrochloride and 100 ml of dry dichloromethane was slowly added dropwise 6.4 g (0.063 mol) of triethylamine under ice-cooling. After the completion of the addition, the mixture was stirred at room temperature for 2 hours and poured into ice/water. Then it was extracted with chloroform and the extract was repeatedly washed with water and dried over magnesium sulfate. After distilling off the solvent, the obtained oily crude product was purified by column chromatography (silica gel, benzene: ethyl acetate=4:1) to thereby give 5.7 g of the title compound compound 5]as a pale yellow, transparent and viscous liquid.

$^1$H-NMR spectrum (60MHz, CDCl$_3$) δ; 0.70~1.90(m,40H), 1.93, 2.00, 2.05 (s×3,9H), 2.40(t,2H), 4.45~4.65 (m,4H), 5.65(m,1H), 7.10~7.30(m,2H), 8.00~8.20(m,2H), 8.45~8.60(m,2H), 8.95~9.00(m,2H)

(ii) 2.8 g (0.005 mol) of 3,4-dihydroxybutyl 2,5,7,8-tetramethyl-2-(4',8',12'-trimethyl-tridecyl)-6-chromanyl carbonate, 1.85 g (0.015 mol) of nicotinic acid, 4.5 g (0.015 mol) of 2-bromo-1-methylpyridinium iodide and 5.6 g of tri-bn-butylamine were added to 60 ml of pyridine. The obtained mixture was stirred by heating to 60° C. for 3 hours. After the completion of the reaction, it was concentrated under reduced pressure. The residue was poured into water and extracted with ether. Then the extract was washed with water and dried over magnesium sulfate. After distilling off the solvent, the obtained brown caramel-like residue was purified by column chromatography (silica gel, benzene : ethyl acetate=4:1) to thereby give 3.1 g of a pale yellow, viscous liquid. This product was identified with the compound 5 obtained in (i).

EXAMPLE 6

2,3-bis(nicotinoyloxy)-1-nicotinoyloxymethylpropyl 2,5,7,8-tetramethyl-2-(4',8', 12'-trimethyl-tridecyl)-6-chromanyl carbonate
[Compound 6]

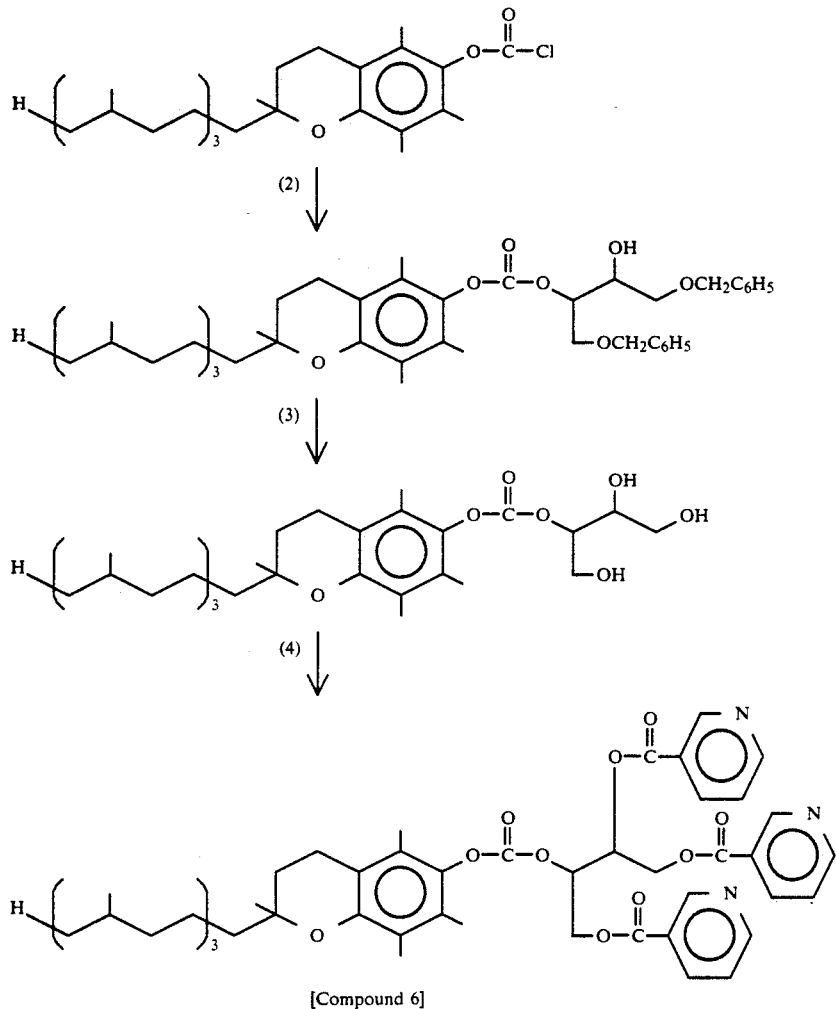

[Compound 6]

(1) Synthesis of 1,4-bis(benzyloxy)-2,3-butanediol

To a solution of 6.0 g (0.022 mol) of 1,4-bis-(benzyloxy)-2-butene in 80 ml of dichloromethane was added 5.4 g (0.022 mol) of m-chloroperbenzoic acid (purity: 70%) in four portions under ice-cooling and stirring. The resulting mixture was stirred at the same temperature for 1 hour. After filtering off the white precipitate thus formed, the filtrate was poured into a 10% aqueous solution of sodium hydrosulfite. The mixture was extracted with dichloromethane, washed with water and dried. After distilling off the solvent, the obtained residue was purified by column chromatography (silica gel, hexane/ether) to thereby give 4.2 g of 1,4-bis(benzyloxy)-2,3-epoxybutane as a colorless liquid.

$^1$H-NMR spectrum (60MHz, CDCl$_3$) δ; 3.1~3.3(m,2H), 3.4~3.6(m,4H), 4.5(s,4H), 7.2(s,10H)

4.2 g of the 1,4-bis(benzyloxy)-2,3-epoxybutane thus obtained was dissolved in a mixture comprising 120 ml of tetrahydrofuran and 30 ml of water. Then 30 ml of an aqueous solution containing 6 ml of 60% perchloric acid was added dropwise thereto under ice-cooling and stirring. After stirring at the same temperature for additional 4 hours, the reaction mixture was poured into ice/water and extracted with ether. The extract was washed with water and dried. After distilling off the solvent, the obtained oily residue was purified by column chromatography (silica gel, hexane/ethyl acetate) to thereby give 2.7 g of 1,4-bis(benzyloxy)-2,3-butanediol as a colorless liquid.

$^1$H-NMR spectrum (60MHz, CDCl$_3$) δ; 3.2(broad s,2H), 3.5(d,4H), 3.7(t,2H), 4.4(s,4H), 7.2(s,10H)

IR (cm$^{-1}$ Nujol) ; 3450 (OH)

(2) Synthesis of 3-benzyloxy-1-benzyloxymethyl-2-hydroxypropyl 2,5,7,8-tetramethyl-2-(4',8', 12'-trimethyltridecyl)-6-chromanyl carbonate 5.0 g (0.01 mol) of α-tocopherol 6-chloroformate was dissolved in 90 ml of ether. To the obtained solution was slowly added dropwise a solution of 3.0 g (0.01 mol) of 1,4-bis(benzyloxy)-2,3-butanediol in 50 ml of pyridine under ice-cooling and stirring. After the completion of the addition, the resulting mixture was further stirred for 4 hours. Then the reaction mixture was poured into 100 ml of diluted hydrochloric acid and extracted with ether. The extract was washed with water and dried over magnesium sulfate. After distilling off the solvent, the obtained oily residue was purified by column chromatography (silica gel, hexane/ethyl acetate) to thereby give 4.4 g of the title compound as a colorless viscous liquid.

$^1$H-NMR spectrum (60MHz, CDCl$_3$) δ; 0.8~1.8(m,38H), 1.95,2.00,2.05 (s×3,9H), 2.5(t,2H), 3.5~3.8(dd, 4H), 3.85(broad,1H), 4.0(m,1H), 4.5 (s,4H), 5.05(m,1H), 7.2(s,10H)

IR (cm$^{-1}$ Nujol) ; 3400 (OH), 1760 (O—CO—O)

(3) Synthesis of 2,3-dihydroxy-1-hydroxymethylpropyl 2,5,7,8-tetramethyl-2-(4',8', 12'-trimethyl-tridecyl)-6-chromanyl carbonate A mixture comprising 4.4 g of 3-benzyloxy-1-benzyloxymethyl-2-hydroxypropyl 2,5,7,8-tetramethyl-2-(4',8', 12'-trimethyltridecyl)-6-chromanyl carbonate, 0.5 g of 5% palladium carbon, 150 ml of ethanol and 5 ml of acetic acid was catalytically reduced in a hydrogen gas stream of 4 kg/cm$^2$ until no hydrogen was absorbed any more (approximately 6 hours). After filtering off the catalyst, the filtrate was concentrated to thereby reduce the amount to approximately ⅓. Then it was poured into water and extracted with ether. The extract was successively washed with an aqueous solution of sodium hydrogencarbonate and water, and dried over magnesium sulfate. After distilling off the solvent, the obtained oily residue was purified by column chromatography (silica gel, hexane : ethyl acetate=2:1) to thereby give 4.3 g of the title compound as a colorless viscous liquid.

$^1$H-NMR spectrum (60MHz, CDCl$_3$) δ; 0.8~1.8(m,38H), 2.00(s,3H), 2.1 (s,6H), 2.5(t,2H), 3.5~3.8(dd,4H), 3.8(broad,3H), 4.0(m,1H), 5.05(m,1H)

(4) Synthesis of 2,3-bis(nicotinoyloxy)-1-nicotinoyloxymethylpropyl 2,5,7,8-tetramethyl-2-(4',8', 12'-trimethyltridecyl)-6-chromanyl carbonate 4.0 g (0.023 mol) of 2,3-dihydroxy-1-hydroxymethylpropyl 2,5,7,8-tetramethyl-2-(4',8', 12'-trimethyltridecyl)-6-chromanyl carbonate was added to 120 ml of dichloromethane and 5.0 g of triethylamine was slowly added thereto under ice-cooling and stirring. The resulting mixture was stirred overnight and then poured into water. The organic phase was collected, repeatedly washed with water and dried over magnesium sulfate. After distilling off the solvent, the obtained residue was purified by column chromatography (silica gel, hexane : ethyl acetate=2:1) to thereby give 3.1 g of the title compound [compound 6] in the form of a white waxy product.

$^1$H-NMR spectrum (60MHz, CDCl$_3$) δ; 0.8~1.8(m,38H), 2.00(s,3H), 2.1 (s,6H), 2.45(t,2H), 4.5~4.8(m,4H), 5.5~5.9(m,2H), 7.0~7.3(m,3H), 7.9~8.2(m,3H), 8.4~8.6(dd,3H), 8.9~9.1(dd,3H)

EXAMPLE 7

2,3,4-Tris(nicotinoyloxy)butyl 2,5,7,8-tetramethyl-2-(4',8',12'-trimethyltridecyl)-6-chromanyl carbonate [Compound 7]

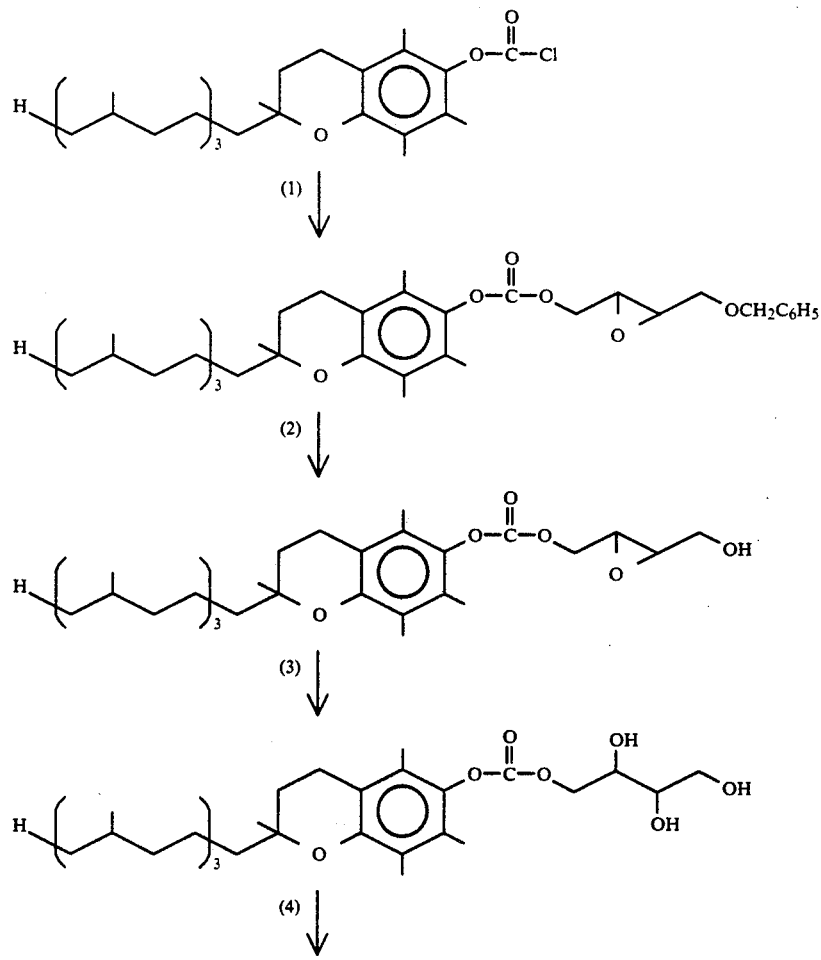

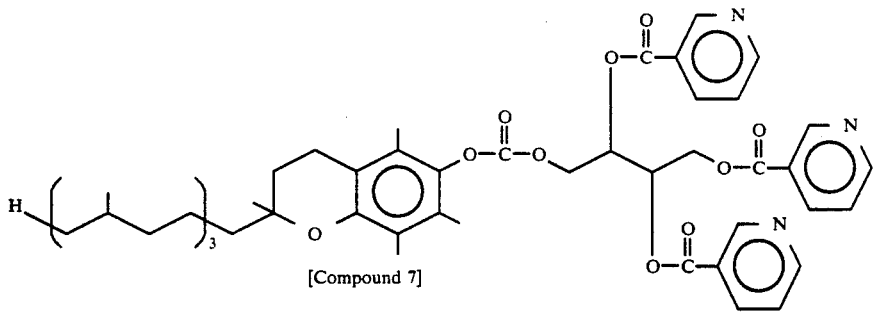

[Compound 7]

(1) Synthesis of 4-benzoyloxy-2,3-epoxybutyl 2,5,7,8-tetramethyl-2-(4',8',12'-trimethyltridecyl)-6-chromanyl carbonate 7.13 g (0.04 mol) of 4-benzyloxy-2-buten-1-ol was dissolved in 250 ml of dichloromethane and 8.6 g (0.04 mol) of m-chloroperbenzoic acid (purity: 80%) was added thereto in four portions under ice-cooling and stirring. After stirring the mixture at the same temperature for additional 1 hour, the precipitate thus formed was filtered off. The filtrate was poured into a 10% aqueous solution of sodium hydrosulfite, extracted with dichloromethane, washed with water, and dried. After distilling off the solvent, the obtained liquid residue was purified by column chromatography (silica gel, hexane/ether) to thereby give 7.7 g of 4-benzyloxy-2,3-epoxybutan-1-ol as a colorless liquid.

$^1$H-NMR spectrum (60MHz, CDCl$_3$) δ; 3.05~3.25(m,2H), 3.4~3.6(m,5H), 4.4(s,2H), 7.15(s,5H)

IR (cm$^{-1}$ Nujol) ; 3450 (OH)

10 0 g (0.02 mol) of α-tocopherol 6-chloroformate was dissolved in 100 ml of ether. To the obtained solution was slowly added dropwise a solution of 4.0 g (0.02 mol) of 4-benzyloxy-2,3-epoxybutan-1-ol in 50 ml of pyridine under ice-cooling and stirring. After the completion of the addition, the mixture was further stirred for 5 hours. Then the reaction mixture was poured into 150 ml of diluted hydrochloric acid, extracted with ether, washed with water, and dried. After distilling off the solvent, the obtained liquid residue was purified by column chromatography (silica gel, hexane/ethyl acetate) to thereby give 10.8 g of the title compound as a pale yellow, viscous liquid.

$^1$H-NMR spectrum (60MHz, CDCl$_3$) δ; 0.8~1.8(m,38H), 2.0(s,3H), 2.1 (s,6H), 2.5(t,2H), 3.1~3.3(m,2H), 3.6(dd,2H), 4.3(dd,2H), 4.5(s,2H), 7.2(s,5H)

(2) Synthesis of 2,3-epoxy-4-hydroxybutyl 2,5,7,8-tetramethyl-2-(4',8',12'-trimethyl-tridecyl)-6-chromanyl carbonate A mixture comprising 6.5 g (0.01 mol) of 4-benzyloxy-2,3-epoxybutyl 2,5,7,8-tetramethyl-2-(4',8', 12'-trimethyltridecyl)-6-chromanyl carbonate, 1 g of 5% palladium carbon, 150 ml of ethanol and 5 ml of acetic acid was catalytically reduced with hydrogen at an initial pressure of 4 kg/cm$^2$ until no hydrogen was absorbed any more (approximately 6 hours). After filtering off the catalyst, the filtrate was concentrated to thereby reduce the amount to ⅓, poured into water and extracted with ether. Then the extract was successively washed with an aqueous solution of sodium hydrogencarbonate and water, and dried. After distilling off the solvent, the obtained oily residue was purifed by column chromatography (silica gel, hexane/ethyl acetate) to thereby give 4.5 g of the title compound as a colorless oily product.

$^1$H-NMR spectrum (60MHz, CDCl$_3$) δ; 0.8~1.8(m,38H), 1.95, 2.00, 2.05 (s×3,9H), 2.5(t,2H), 2.8(broad, 1H), 3.1~3.4(m,2H), 3.7(d,2H), 4.3(d,2H)

IR (cm$^{-1}$ Nujol); 3450 (OH), 1760 (O—CO—O)

(3) Synthesis of 2 3,4-trihydroxybutyl 2,5,7,8-tetramethyl-2-(4',8', 12'-trimethyltridecyl)-6-chromanyl carbonate 4.0 g (0.0073 mol) of 2,3-epoxy-4-hydroxybutyl 2,5,7,8-tetramethyl-2-(4',8', 12'-trimethyltridecyl)-6-chromanyl carbonate was dissolved in a mixture of 140 ml of tetrahydrofuran with 50 ml of water. To the obtained solution was slowly added dropwise 30 ml of an aqueous solution containing 10 ml of 60% perchloric acid under ice-cooling and stirring. After stirring at 5 to 10° C for additional 5 hours, the reaction mixture was poured into water and extracted with ether. Then the extract was washed with water and dried over magnesium sulfate. After distilling off the solvent, the obtained residue was purified by column chromatography (silica gel, hexane : ethyl acetate =3 : 1) to thereby give 2.6 g of the title compound as a pale yellow and starch syrup-like product.

$^1$H-NMR spectrum (60MHz, CDCl$_3$) δ; 0.8~1.8(m,38H), 1.95, 2.00, 2.05 (s×3, 9H), 2.45(t,2H), 2.8~3.1 (broad,3H), 3.6~4.2(m,4H), 4.3 (d,2H)

IR (cm$^{-1}$ Nujol) ; 3400 (OH), 1760 (O—CO—O) (4) Synthesis of 2,3,4-tris(nicotinoyloxy)butyl 2,5,7,8-tetramethyl-2-(4',8', 12'-trimethyl-tridecyl)-6-chromanyl carbonate 2.4 g (0.0042 mol) of 2,3,4-trihydroxybutyl 2,5,7,8-tetramethyl-2-(4',8', 12'-trimethyl-tridecyl)-6-chromanyl carbonate and 3.0 g (0.017 mol) of nicotinoyl chloride hydrochloride were added to 100 ml of dichloromethane. To the obtained solution was slowly added dropwise 3.5 g of triethylamine under ice-cooling and stirring. After stirring overnight, the reaction mixture was poured into water and extracted with dichloromethane. Then the extract was washed with water and dried. After distilling off the solvent, the obtained residue was purified by column chromatography (silica gel, hexane/ethyl acetate =3 : to thereby give 2.0 g of the title compound compound 7]as a white waxy product.

$^1$H-NMR spectrum (60MHz, CDCl$_3$) δ; 0.8~1.8(m,38H), 1.98(s,3H), 2.05 (s,6H), 2.50(t,2H), 4.7(m,4H), 5.9 (m,2H), 7.2(m,3H), 8.1~8.2(m,3H), 8.6(dd,3H), 9.0(dd,1H), 9.1(dd,2H)

IR (cm$^{-1}$ Nujol) ; 1730 (COOAr), 1760 (O—CO—O)

EXAMPLE 8

2,2-Bis(nicotinoyloxymethyl)propyl 2,5,7,8-tetramethyl-2-(4',8', 12'-trimethyltridecyl)-6-chromanyl carbonate
[Compound 8]

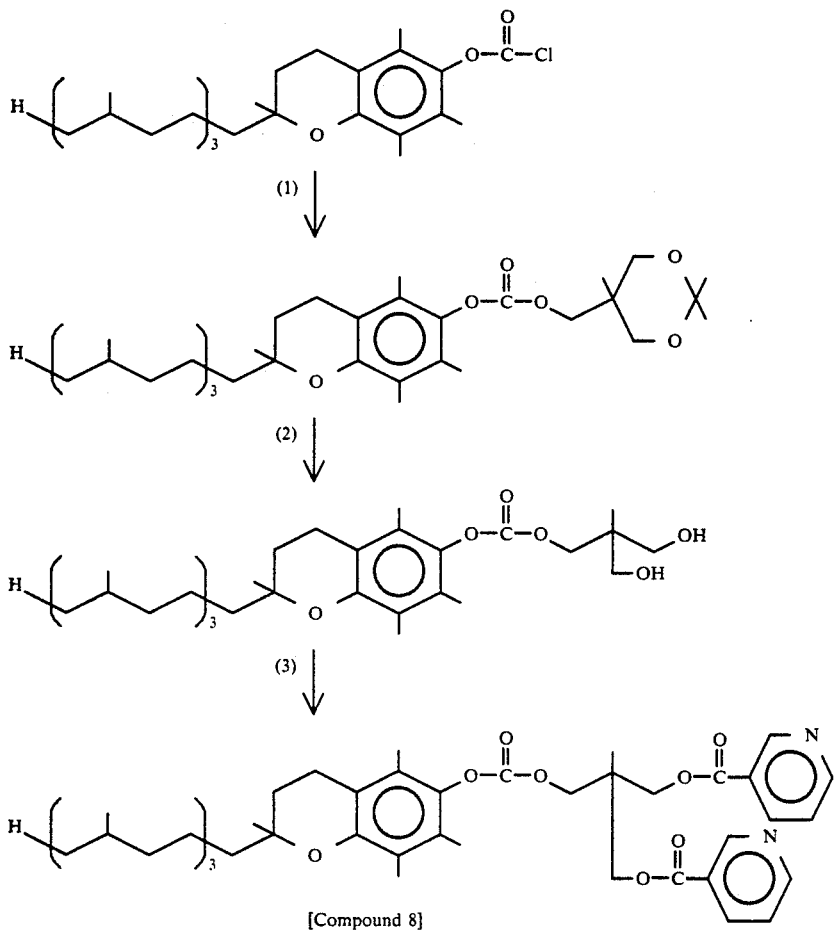

[Compound 8]

(1) Synthesis of 2,2,5-trimethyl-1,3-dioxan-5-ylmethyl 2,5,7,8-tetramethyl-2-(4',89',12'-trimethyltridecyl)-6-chromanyl carbonate 20.0 g (0.17 mol) of 2,2-bis(hydroxymethyl)-propan-1-ol was dissolved in a mixture of 100 ml of acetone, 50 ml of benzene and 50 ml of petroleum ether. 0.5 g of p-toluenesulfonic acid was added thereto and the resulting mixture was boiled by heating. Then the mixture was refluxed for approximately 8 hours while removing the water thus formed. After cooling, 10 g of potassium acetate was added thereto and the mixture was stirred for 20 minutes. After filtering off inorganic matters, the obtained colorless transparent filtrate was concentrated. Thus 24.5 g of a crude product of 2,2,5-trimethyl-1,3-dioxan-5-ylmethanol was obtained. This product possessed a high purity and thus used in the subsequent reaction as such.

$^1$H-NMR spectrum (60MHz, CDCl$_3$) δ; 0.80(s,3H), 1.34, 1.37(s×2, 6H), 3.0 (broad, 1H), 3.5(s,6H)

To a mixture comprising 3.8 g (0.024 mol) of the 2,2,5-trimethyl-1,3-dioxan-5-ylmethanol obtained above, 14 ml of pyridine and 50 ml of dichloromethane was added dropwise a solution of 9.8 g (0.02 mol) of α-tocopherol 6-chloroformate in 40 ml of dichloromethane within 50 minutes under stirring at room temperature. The reaction mixture was further stirred at room temperature for 20 hours and then extracted with 300 ml of ethyl acetate and 100 ml of 2 N hydrochloric acid. The extract was washed with water and dried over magnesium sulfate. After distilling off the solvent, the obtained residue was purified by column chromatography (silica gel, benzene). Thus 10.3 g of the title compound was obtained as a pale yellow, viscous liquid.

$^1$H-NMR spectrum (60MHz, CDCl$_3$) δ; 0.8~1.9(m,47H), 1.95(s,3H), 2.05 (s,6H), 2.5(t,2H), 3.55(s,4H), 4.23 (s,2H)

IR (cm$^{-1}$ Liq. film); 1760 (OH)

(2) Synthesis of 2,2-bis(hydroxymethyl)propyl 2,5,7,8-tetramethyl-2-(4',8', 12'-trimethyl-tridecyl)-6-chromanyl carbonate 10 g of 2,2,5-trimethyl-1,3-dioxan-5-ylmethyl 2,5,7,8-tetramethyl-2-(4',8', 12'-trimethyl-tridecyl)-6-chromanyl carbonate was dissolved in a mixture of 70 ml of 2 N hydrochloric acid and 35 ml of methanol and heated under reflux for 4.5 hours. After cooling, the reaction mixture was extracted with 500 ml of ethyl acetate and 400 ml of water. The extract was washed with water, dried and concentrated. Then the obtained residue was purified by column chromatography (silica gel, hexane/ethyl acetate). Thus 7.4 g of the title compound was obtained as a colorless and starch syrup-like product.

¹H-NMR spectrum (60MHz, CDCl₃) δ;
Synthesis 2-bi 0.8~1.9(m,41H), 1.95(s,3H), 2.05 (s,6H), 2.55(t,2H), 2.9(brosd,2H), 3.0(broad s,4H), 4.24(s,2H)

(3) of 2, s(nicotinoyloxymethyl)propyl 2,5,7,8-tetramethyl-2-(4',8', 12'-trimethyl-tridecyl)-6-chromanyl carbonate 7.0 g (0.01 mol) of 2,2-bis(hydroxymithyl)propyl 2,5,7,8-tetramethyl-2-(4',8', 12'-trimethyltridecyl)-6-chromanyl carbonate and 8.6 g (0.04 mol) of nicotinoyl chloride hydrochloride were suspended in 100 ml of dichloromethane. To the obtained suspension was slowly added dropwise 9.7 g of triethylamine under ice-cooling and stirring. After the completion of the addition, the reaction mixture was stirred at room temperature for 20 hours, poured into water, and extracted with ethyl acetate. The extract was washed with water and dried over magnesium sulfate. After distilling off the solvent, the obtained residue was purified by column chromatography (silica gel, hexane ethyl acetate=2:1). Thus 8.0 g of the title compound [compound 8] was obtained as a pale yellow, viscous liquid.

¹H-NMR spectrum (60MHz, CDCl₃) δ;
0.8~1.9(m,41H), 1.92, 1.96, 2.05 (s,×3,9H), 2.5(t,2H), 4.32, 4.36 (s×2,6H), 7.1~7.3(m,2H), 7.96~8.20(m,2H), 8.5~8.62(m, 2H), 8.96 ~9.10(m,2H)

EXAMPLE 9

3-Methyl-2,3-bis(nicotinoyloxy)butyl 2,5,7,8-tetramethyl-2-(4',8',12'-trimethyltridecyl)-6-chromanyl carbonate [Compound 9]

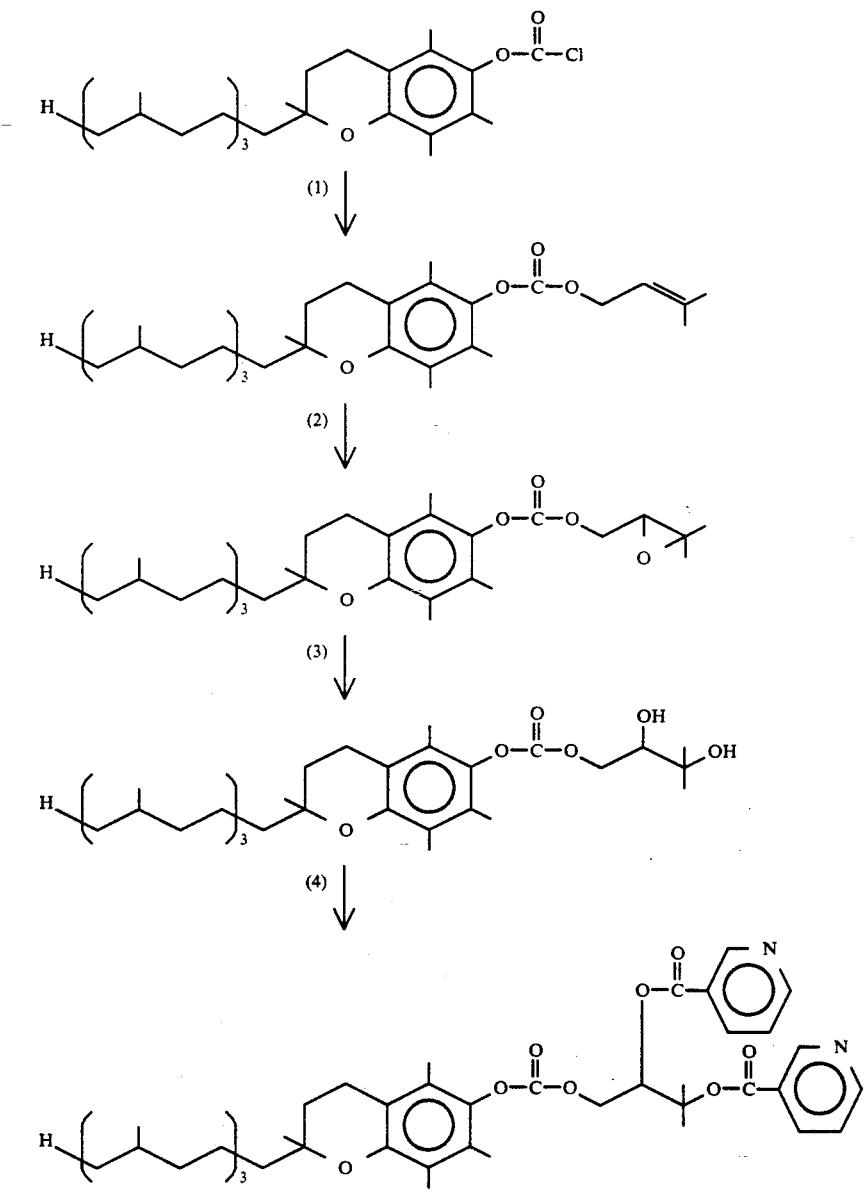

[Compound 9]

(1) Synthesis of 3-methyl-2-butenyl 2,5,7,8-tetramethyl-2-(4',8',12'-trimethtyltridecyl)-6-chromanyl carbonate 1.8 g (0.02 mol) of 3-methyl-2-buten-1-ol was dissolved in 20 ml of pyridine. To the obtained solution was slowly added dropwise 30 ml of a solution of 10.0 g (0.02 mol) of α-tocopherol 6-chloroformate in ether under ice-cooling and stirring. After stirring at the same temperature for 2 hours, the reaction mixture was poured into diluted hydrochloric acid and extracted with ether. The extract was washed with water and dried. After distilling off the solvent, the obtained pale yellow, oily residue was purified by column chromatography (silica gel, hexane ethyl acetate=4:1). Thus 10.2 g of the title compound was obtained as a colorless viscous liquid.

$^1$H-NMR spectrum (60MHz, CDCl$_3$) δ; 0.8~1.9(m,38H), 1.75(s,6H), 1.96, 2.00,205(s×3,9H), 2.45(t,2H) 4.60(d,2H), 5.4(t,1H)

IR (cm$^{-1}$ Liq. film) ; 1760 (O—CO—O)

(2) Synthesis of 2,3-epoxy-3-methylbutyl 2,5,7,B-tetramethyl-2-(4',8', 12'-trimethyltridecyl)-6-chromanyl carbonate 9.7 g (0.018 mol) of 3-methyl-2-butenyl 2,5,7,8-tetramethyl-2-(4',8', 12'-trimethyltridecyl)-6-chromanyl carbonate was dissolved in 100 ml of dichloromethane. To the obtained solution was added 4.3 g (0.02 mol) of m-chloroperbenzoic acid (purity: 80%) under ice-cooling and stirring. The mixture was then stirred at the same temperature for 1 hour. After filtering off the white precipitate thus formed, the filtrate was poured into an aqueous solution of sodium hydrosulfite and extracted with dichloromethane. The extract was washed with water and dried. After distilling off the solvent, the obtained oily residue was purified by column chromatography (silica gel, hexane : ethyl acetate=5:1). Thus 9.1 g of the title compound was obtained as a colorless viscous liquid.

$^1$H-NMR spectrum (60MHz, CDCl$_3$) δ; 0.8~1.8(m,44H), 2.0(s,3H), 2.1 (s,6H), 2.45(t,2H), 3.0(t,1H), 4.2 (dd,2H)

IR (cm$^{-1}$ Liq. film); 1760 (O—CO—O)

(3) Synthesis of 2,3-dihydroxy-3-methylbutyl 2,5,7,8-tetramethyl-2-(4',8', 12'-trimethyltridecyl)-6-chromanyl carbonate 8.5 g of 2,3-epoxy-3-methylbutyl 2,5,7,8-tetra-methyl-2-(4',8', 12'-trimethyltridecyl)-6-chromanyl carbonate was added to 300 ml of tetrahydrofuran and 150 ml of water. To the resulting mixture was slowly added dropwise a solution obtained by diluting 60% of perchloric acid with 20 ml of water under ice-cooling and stirring. After the completion of the addition, the reaction mixture was further stirred for additional 4 hours and then poured into ice/water, followed by extracting with ether. The extract was washed with water and dried. After distilling off the solvent, the obtained oily residue was purified by column chromatography (silica gel, benzene : ethyl acetate=8:1). Thus 5.4 g of the title compound was obtained as a colorless viscous liquid.

$^1$H-NMR spectrum (60MHz, CDCl$_3$) δ; 0.8~1.8(m,44H), 1.95(s,3H), 2.1 (s,6H), 2.45(t,2H), 3.2~4.0(m,5H)

IR (cm$^{-1}$ Liq. film); 1760 (O—CO—O), 3400 (OH)

(4) Synthesis of 3-bis(nicotinoyloxy)butyl 2,5,7,8-tetramethyl-2-(4',8', 12'-trimethyl-tridecyl)-6-chromanyl carbonate 2.2 g (0.0038 mol) of 2,3-dihydroxy-3-methylbutyl 2,5,7,8-tetramethyi-2-(4',8', 12'-trimethyltridecyl)-6-chromanyl carbonate and 2 g (0.02 mol) of triethylamine were dissolved in 50 ml of dichloromethane. To the obtained solution was added 2.6 g (0.0144 mol) of nicotinoyl chloride hydrochloride in three portions under ice-cooling and stirring. Then the mixture was stirred at the same temperature for additional 2 hours and poured into water, followed by extracting with ether. The extract was washed with water and dried. After distilling off the solvent, the obtained yellow oily residue was purified by column chromatography (silica gel, benzene : ethyl acetate =5 : 1). Thus 1.5 g of the title compound [compound 9]was obtained as a pale yellow, viscous liquid.

$^1$H-NMR spectrum (60MHz, CDCl$_3$) δ; 0.8~1.8(m,44H), 1.95(s,3H), 2.1 (s,6H), 2.45(t,2H), 4.6(d,2H), 5.5 ~5.8(m,1H), 7.3~7.5(m,2H), 8.1 (dd,2H), 8.5(dd,2H), 9.0(d,2H)

IR (cm$^{-1}$ Liq. film) ; 1760, 1730 (O—CO—O, COOAr)

EXAMPLE 10

4-Nicotinoyloxy-3-nicotinoyloxymethylbutyl 2,5,7,8-tetramethyl-2-(4',8', 12'-trimethyltridecyl)-6-chromanyl carbonate [Compound 10]

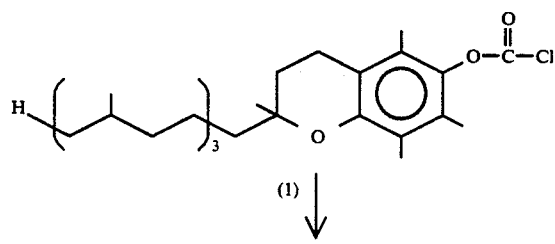

(1)

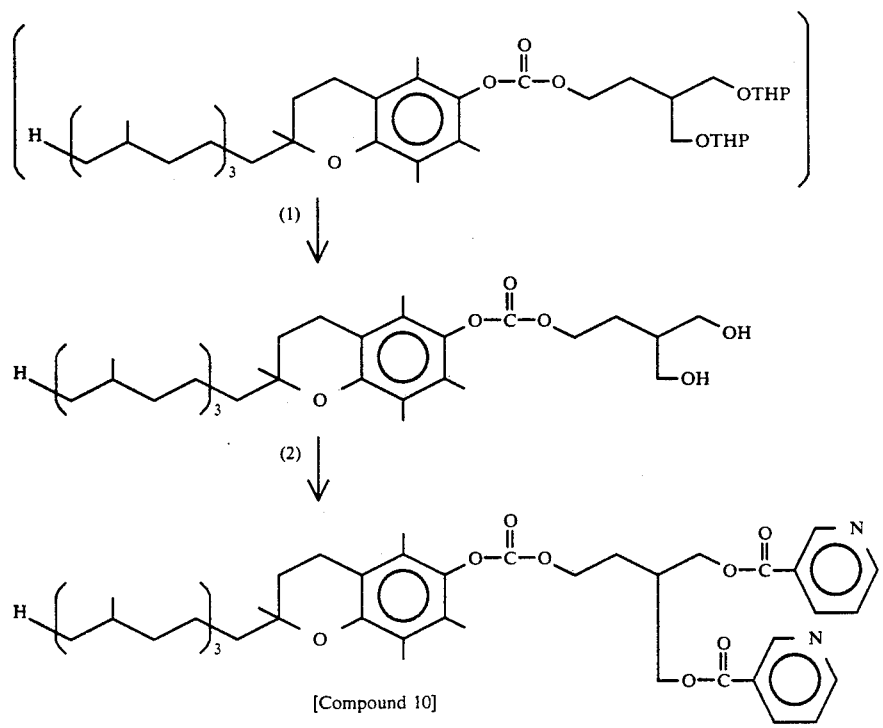

[Compound 10]

(1) Synthesis of 4-hydroxy-3-hydroxymethylbutyl 2,5,7,8-tetramethyl-2-(4',8', 12'-trimethyl tridecyl)-6-chromanyl carbonate To a solution comprising 11.4 g (0.04 mol) of 4-(2-tetrahydropyranyloxy)-3-(2-tetrahydropyranyl-oxymethyl)butan-1-ol, 5.5 g (0.07 mol) of pyridine and 90 ml of dichloromethane was added dropwise a solution of 19.9 g (0.04 mol) of α-tocopherol 6-chloroformate in 50 ml of dichloromethane under ice-cooling and stirring within 30 minutes. The reaction mixture was further stirred at room temperature overnight. After concentrating the reaction mixture under reduced pressure, the obtained residue was dissolved in 500 ml of ether, washed with water and dried. After distilling off the solvent, 28.7 g of 4-(2-tetra-hydropyranyloxy)-3-(2-tetrahydro-pyranyloxymethyl)-butyl 2,5,7,8-tetramethyl-2-(4',8', 12'-trimethyl-tridecyl)-6-chromanyl carbonate was obtained as a pale yellow, viscous liquid. This product was highly pure and thus used in the subsequent step as such without carrying out any purification treatment.

27.5 g (0.037 mol) of the 4-(2-tetrahydro-pyranyloxy)-3-(2-tetrahydropyranyloxymethyl)butyl 2,5,7,8-tetramethyl-2-(4',8', 12'-trimethyltridecyl)-6-chromanyl carbonate prepared in the above step was dissolved in 300 ml of methanol. To the obtained solution was added 5 g of p-toluenesulfonic acid followed by stirring at room temperature for 1 hour. 1 l of water was added to the reaction mixture and the oily matter thus separated out was extracted with ether. The extract was washed with water and dried. After distilling off the solvent, the obtained oily residue was purified by column chromatography (silica gel, hexane : ethyl acetate=3:1). Thus 16.5 g of the title compound was obtained as a colorless viscous liquid.

$^1$H-NMR spectrum (60MHz, CDCl$_3$) δ; 0.8~1.8(m,41H), 1.95(s,3H), 2.1 (s,6H), 2.50(t,2H), 2.95(broad,2H), 3.72(s,4H), 4.1~4.4(m,2H)

IR (cm$^{-1}$ Liq. film); 1760 (O—CO—O), 3400 (OH)

(2) Synthesis of 4-nicotinoyloxy-3-nicotinoyloxy-methylbutyl 2,5,7,8-tetramethyl-2-(4',8', 12'-trimethyltridecyl)-6-chromanyl carbonate 1.6 g (0.03 mol) of 4-hydroxy-3-hydroxymethyl-butyl 2,5,7,8-tetramethyl-2-(4',8', 12'-trimethyl-tridecyl)-6-chromanyl carbonate and 1.5 g (0.09 mol) of nicotinoyl chloride hydrochloride were added to 40 ml of dichloromethane. To the obtained mixture was slowly added dropwise 2.3 g of triethylamine under ice-cooling and stirring. After the completion of the addition, the mixture was further stirred at room temperature for 6 hours and poured into water followed by extracting with dichloromethane. The extract was washed with water and dried. After distilling off the solvent, the obtained oily residue was purified by column chromatography (silica gel, chloroform). Thus 1.7 g of the title compound [compound 10] was obtained as a colorless viscous liquid.

$^1$H-NMR spectrum (60MHz, CDCl$_3$) δ; 0.8~1.8(m,41H), 1.97(s,3H), 2.1 (s,6H), 2.50(t,2H), 4.3(m,2H), 4.45 (d,4H), 7.1~7.3(m,2H), 8.05(m,2H), 8.5(m,2H), 9.0(m,2H)

IR (cm$^{-1}$ Liq. film); 1758, 1725 (O—CO—O, COOAr)

EXAMPLE 11

2-Methyl-2,4-bis(nicotinoyloxy)butyl 2,5,7,8-tetramethyl-2-(4',8', 12'-trimethyltridecyl)-6-chromanyl carbonate
[Compound 11]

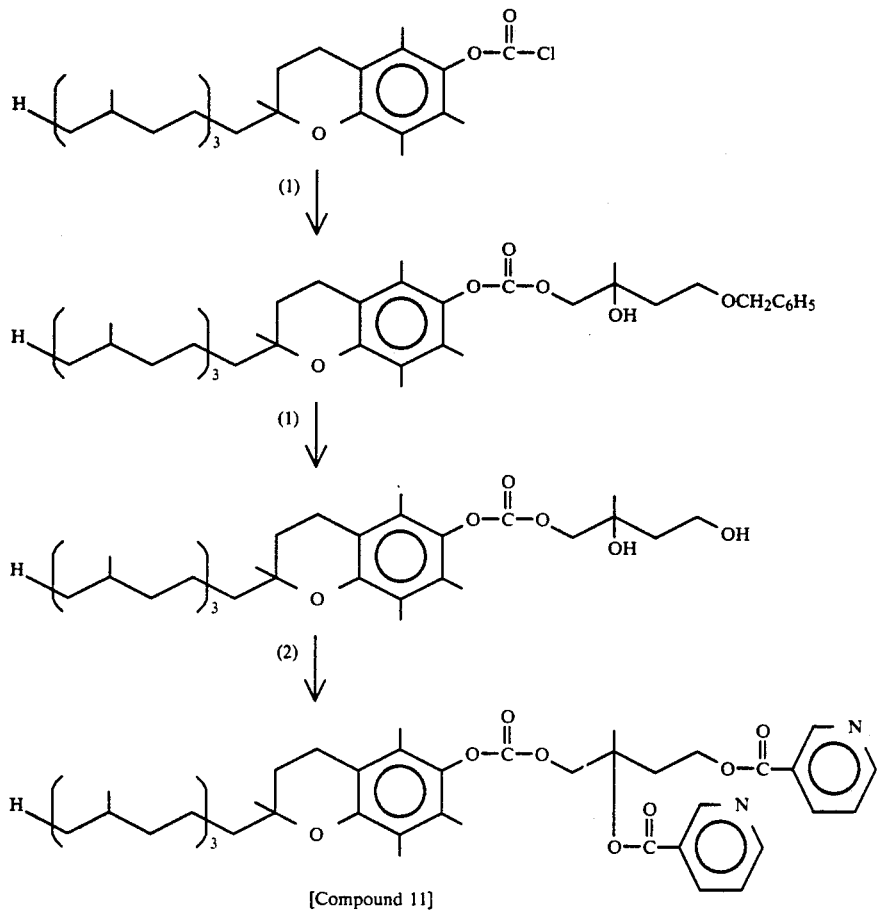

[Compound 11]

2,5,7,8-tetramethyl-2-(4',8', 12'-trimethyl-tridecyl)-6-chromanyl carbonate 4.4 g (0.022 mol) of 4-benzyloxy-2-hydroxy-2-methyl-butan-1-ol was dissolved in 50 ml of pyridine. To the obtained solution was added dropwise a solution of 10.8 g (0.022 mol) of α-tocopherol 6-chloroformate in 100 ml of ether within 30 minutes under ice-cooling and stirring. The reaction mixture was further stirred under ice-cooling for 2 hours. Next, the reaction mixture containing a precipitate of pyridine hydrochloride was poured into diluted hydrochloric acid and extracted with ether. The extract was washed with water and dried. After distilling off the solvent, the obtained oily residue was purified by column chromatography (silica gel, hexane : benzene = 5:1). Thus 11.0 g of 4-benzyloxy-2-hydroxy-2-methylbutyl 2,5,7,8-tetramethyl-2-(4',8',12'-trimethyltridecyl)-6-chromanyl carbonate was obtained as a colorless viscous liquid.

IR (cm$^{-1}$ Liq. film); 1760 (O—CO—O), 3450 (OH)

10.0 g (0.01 mol) of the 4-benzyloxy-2-hydroxy-2-methylbutyl 2,5,7,8-tetramethyl-2-(4',8', 12'-trimethyl-tridecyl)-6-chromanyl carbonate obtained in the above step, 2.0 g of palladium carbon, 200 ml of ethanol and 10 ml of acetic acid were mixed together. The obtained mixture was then catalytically reduced under a hydrogen pressure of 4 kg/cm$^2$ for 6 hours. After the completion of the reduction, the catalyst was filtered off and the filtrate was concentrated to thereby reduce the amount to approximately ⅓, poured into water, and extracted with ether. The extract was washed with water and dried. AFter distilling off the solvent, the obtained oily residue was purified by column chromatography (silica gel, hexane : ethyl acetate = 3:1). Thus 8.7 g of the title compound was obtained as a colorless viscous liquid.

$^1$H-NMR spectrum (60 MHz, CDCl$_3$) δ; 0.8~1.8(m,43H), 1.95(s,3H), 2.1 (s,6H), 2.50(t,2H), 3.3~4.3(m,6H)

IR (cm$^{-1}$ Liq. film); 1760 (O—CO—O), 3500 (OH)

(2) Synthesis of 2-methyl-2,4-bis(nicotinoyloxy)-butyl 2,5,7,8-tetramethyl-2-(4',8',12'-trimethylridecyl)-6-chromanyl carbonate 5.2 g (0.009 mol) of 2,4-dihydroxy-3-ethylbutyl 2,5,7,8-tetramethyl-2-(4',8',12'-trimethyltridecyl)-6-chromanyl carbonate and 4.8 g (0.027 mol) of nicotinoyl chloride hydrochloride were added to 100 ml of dichloromethane. To the obtained mixture was slowly added dropwise 6 g of triethylamine under ice-cooling and stirring. After the completion of the addition, the reaction mixture was further stirred at room temperature for 6 hours, then poured into water and extracted with dichloromethane. The extract was washed with water and dried. After distilling off the solvent, the obtaind oily residue was purified by column chromatography (silica gel, chloroform). Thus 5.5 g of the title compound [compound 11] was obtained as a white waxy product.

¹H-NMR spectrum (60MHz, CDCl₃) δ; 0.8~1.8(m,43H), 1.95(s,3H), 2.0 (s,6H), 2.5(t,2H), 3.3~3.8(m,4H), 7.1~7.3(m,2H), 8.0~8.3(m,2H), 8.6(dd,2H), 9.0(dd,2H)

IR (cm⁻¹ Liq. film) ; 1760, 1740 (O—CO—O, COOAr)

EXAMPLE 12

3-Methyl-3,4-bis(nitocinoyloxy)butyl 2,5,7,8-tetramethyl-2-(4',8',12'-trimethyltridecyl)-6-chromanyl carbonate [Compound 12]

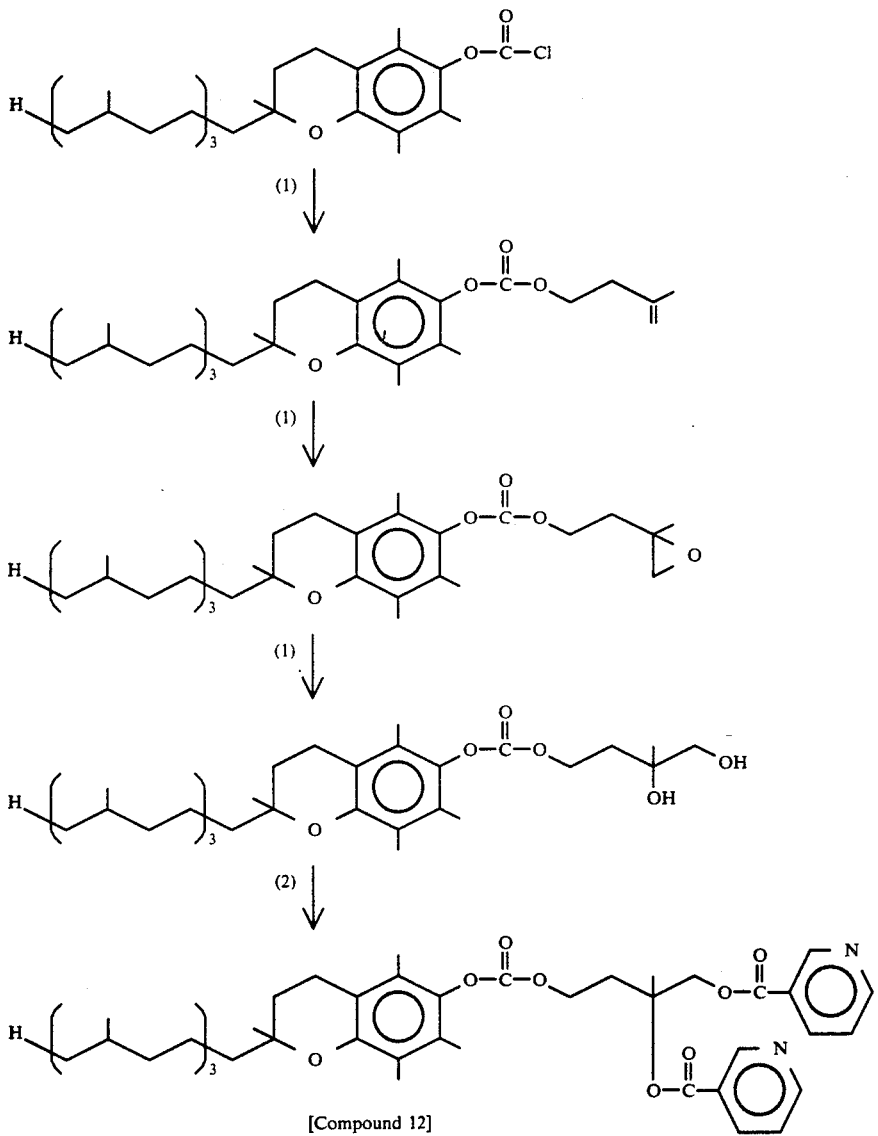

[Compound 12]

(1) Synthesis of 3,4-dihydroxy-3-methylbutyl 2,5,7,8-tetramethyl-2-(4',8', 12'-trimethyl-tridecyl)-6-chromanyl carbonate 2.0 g (0.023 mol) of 3-methyl-3-buten-1-ol was dissolved in 20 ml of pyridine. To the obtained solution was added dropwise a solution of 10.0 g (0.02 mol) of α-tocopherol 6-chloroformate in 50 ml of ether within 30 minutes under ice-cooling and stirring. The resulting mixture was further stirred under ice-cooling for 2 hours. Then the reaction mixture containing a precipitate of pyridine hydrochloride was poured into diluted hydrochloric acid and extracted with ether. The extract was washed with water and dried. After distilling off the solvent, the obtained oily residue was purified by column chromatography (silica gel, hexane : benzene =5 : 1). Thus 9.2 g of 3-methyl-3-butenyl 2,5,7,8-tetramethyl-2-(4',8', 12'-trimethyltridecyl)-6-chromanyl carbonate was obtained as a colorless viscous liquid.

IR (cm⁻¹ Liq. film) ; 1760 (O—CO—O)

8.2 g (0.015 mol) of the 3-methyl-3-butenyl 2,5,7,8-tetramethyl-2-(4',8', 12'-trimethyltridecyl)-6-chromanyl carbonate obtained in the above step was dissolved in 200 ml of dichloromethane. To the obtained solution was added 4.0 g (0.0185 mol) of m-chloroperbenzoic acid (purity: 80%) in four portions under ice-cooling and stirring. Then the mixture was further stirred at the same temperature for 1 hour. After filtering off the white precipitate thus formed, the filtrate was poured into an aqueous solution of sodium hydrosulfite and extracted with 200 ml of dichloromethane. The extract was washed with water and dried. After distilling off the solvent, the obtained oily residue was purified by column chromatography (silica gel, hexane/ether). Thus 8.3 g of 3,4-epoxy-3-methylbutyl-2,5,7,8-tetramethyl-2-(4',8', 12'-trimethyltridecyl)-6-chromanyl carbonate was obtained as a colorless viscous liquid.
0.8~1.8(m,43H0), 2.0(s,3H), 2.1 (s,6H), 2.45(t,2H), 2.6(t,2H), 4.3 (t,2H)

IR (cm$^{-1}$ Liq. film); 1760 (O—CO—O)

7.2 g (0.013 mol) of the 3,4-epoxy-3-methylbutyl 2,5,7,8-tetramethyl-2-(4',8', 12'-trimethyltridecyl)-6-chromanyl carbonate, 200 ml of tetrahydrofuran and 50 ml of water were mixed together. To the obtained mixture was slowly added dropwise 30 ml of an aqueous solution containing 12 ml of 60% perchloric acid under ice-cooling and stirring. After the completion of the addition, the mixture was further stirred for 3 hours and then poured into ice/water. After confirming that no peroxide remained with potassium iodide starch paper, the mixture was extracted with 500 ml of ether. The extract was washed with water and dried. After distilling off the solvent, the obtained oily residue was purified by column chromatography (silica gel, benzene : ethyl acetate=8:2). Thus 5.4 g of the title compound was obtained as a colorless viscous liquid.

$^1$H-NMR spectrum (60 MHz, CDCl$_3$) δ; 0.8~1.8(m,43H), 1.95(s,3H), 2.0 (s,6H), 2.45(t,2H), 3.8(s,2H), 3.9~4.2(m,4H)

IR (cm$^{-1}$ Liq. film); 1760 (O—CO—O), 3450 (OH)

(2) Synthesis of 3-methyl-3,4-bis(nicotinoyloxy)-butyl 2,5,7,8-tetramethyl-2-(4',8',12'-trimethyltridecyl)-6-chromanyl carbonate 2.9 g (0.005 mol) of 3,4-dihydroxy-3-methylbutyl 2,5,7,8-tetramethyl-2-(4',8',12'-trimethyltridecyl)-6-chromanyl carbonate and 2.7 g (0.015 mol) of nicotinoy chloride hydrochloride were added to 100 ml of dichloromethane. To the obtained mixture was slowly added dropwise 6 g of triethylamine. After the completion of the addition, the mixture was further stirred at room temperature for 6 hours, then poured into water and extracted with dichloromethane. The extract was washed with water and dried. After distilling off the solvent, the obtained oily residue was purified by column chromatography (silica gel, chloroform). Thus 2.3 g of the title compound [compound 12]was obtained as a colorless viscous liquid.

$^1$H-NMR spectrum (60 MHz, CDCl$_3$) δ; 0.8~1.8(m,43H), 2.0(s,3H), 2.1(s,6H), 2.4(t,2H), 2.6(t,2H), 2.9(s,2H), 7.3(m,2H), 8.1(m,2H), 8.6(dd,2H), 9.1(d,2H)

IR (cm$^{-1}$ Liq.film); 1760, 1730 (O—CO—O, COOAr)

EXAMPLE 13

3-Nicotinoyloxy-2,2-bis(nicotinoyloxymethyl)propyl 2,5,7,8-tetramethyl-2-(4',8',12'-trimethyltridecyl)-6-chromanyl carbonate [Compound 13]

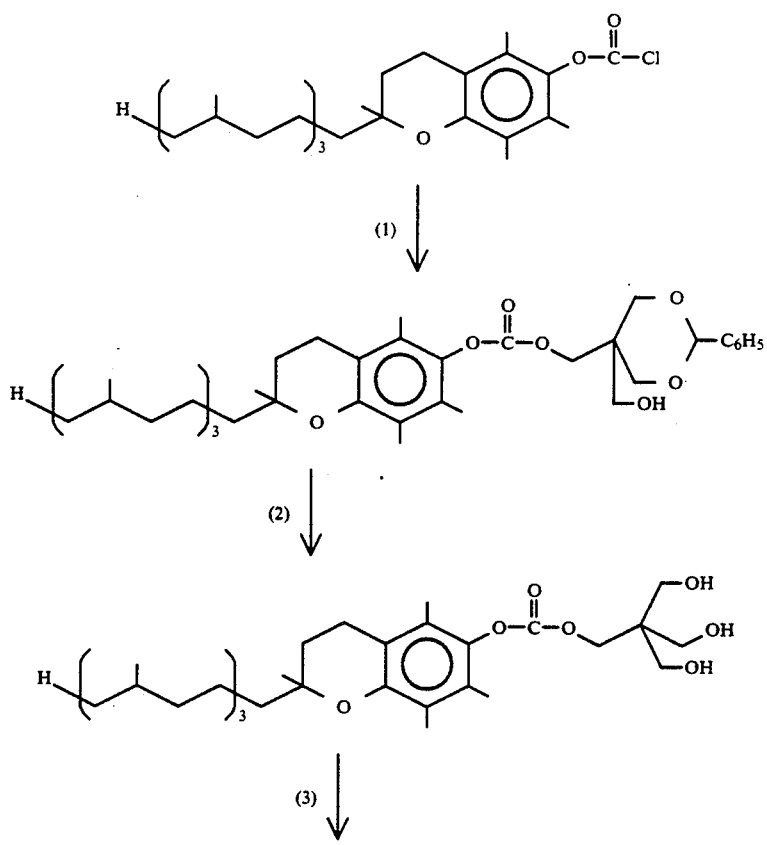

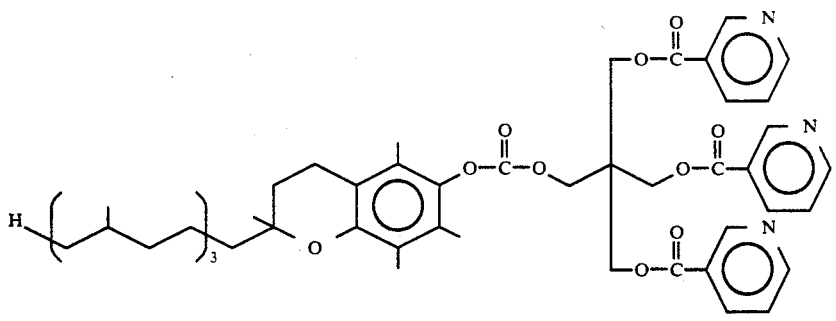

[Compound 13]

(1) Synthesis of 5-hydroxymethyl-2-phenyl-1,3-dioxan-5-ylmethyl 2,5,7,8-tetramethyl-2-(4',8',12'-trimethyltridecyl)-6-chromanyl carbonate 2.2 g (0.01 mol) of monobenzalpentaerythritol and 1.2 g (0.015 mol) of pyridine were dissolved in 100 ml of dichloromethane. To the obtained solution was added dropwise a solution of 4.9 g (0.01 mol) of α-tocopherol 6-chloroformate in 20 ml of dichloromethane within 30 minutes under ice-cooling and stirring. After the completion of the addition, the mixture was further stirred under ice-cooling for 2 hours. Then the reaction mixture containing a precipitate of pyridine hydrochloride was poured into diluted hydrochloric acid and extracted with dichloromethane. The extract was washed with water and dried. After distilling off the solvent, the obtained oily residue was purified by column chromatography (silica gel, chloroform). Thus 5.5 g of the title compound was obtained as a pale yellow, viscous liquid.

$^1$H-NMR spectrum (60 MHz, CDCl$_3$) δ; 0.8~1.8(m,38H), 2.0(s,3H), 2.1(s,6H), 2.5(t,2H), 3.2~4.2(m,8H), 4.65(s,1H), 5.3(m,1H), 7.2~7.3(m,5H)

IR (cm$^{-1}$ Liq.film); 1755 (O—CO—O), 3450 (OH)

(2) Synthesis of 3-hydroxy-2,2-bis(hydroxymethyl)propyl 2,5,7,8-tetramethyl-2-(4',8',12'-trimethyltridecyl)-6-chromanyl carbonate 5.3 g of 5-hydroxymethyl-2-phenyl-1,3-dioxan-5-ylmethyl 2,5,7,8-tetramethyl-2-(4',8',12'-trimethyltridecyl)-6-chromanyl carbonate was dissolved in 50 ml of acetic acid. To the obtained solution was added 0.3 g of 10% palladium carbon. Then the mixture was catalytically reduced under a hydrogen pressure of 3 kg/cm$^2$. After filtering off the catalyst, the filtrate was poured into water. The oily matter thus precipitated was extracted with ether. The extract was successively washed with water, an aqueous solution of sodium hydrogencarbonate and water, and dried. After distilling off the solvent, 4.5 g of a colorless and resinous product was obtained. It was purified by column chromatography (silica gel, benzene:ethyl acetate=1:1). Thus 3.7 g of the title compound was obtained as a colorless waxy solid.

$^1$H-NMR spectrum (60 MHz, CDCl$_3$) δ; 0.8~1.8(m,38H), 2.0(s,3H), 2.1(s,6H), 2.5(t,2H), 3.6(m,9H), 4.2(s,2H)

IR (cm$^{-1}$ Liq.film); 1760 (O—CO—O), 3450 (OH)

(3) Synthesis of 3-nicotinoyloxy-2,2-bis-(nicotinoyloxymethyl)propyl 2,5,7,8-tetramethyl-2-(4',8',12'-trimethyltridecyl)-6-chromanyl carbonate 3.55 g (0.006 mol) of 3-hydroxy-2,2-bis-(hydroxymethyl)propyl 2,5,7,8-tetramethyl-2-(4',8',12'-trimethyltridecyl)-6-chromanyl carbonate, 4.4 g (0.036 mol) of nicotinic acid, 10.8 g (0.036 mol) of 1-methyl-2-bromopyridinium iodide and 11.2 g (0.06 mol) of tri-n-butylamine were added to 50 ml of pyridine and the obtained mixture was stirred at 50° C. for approximately 2 hours in a nitrogen gas stream. After distilling off the pyridine under reduced pressure, the residue was extracted with ether. The extract was washed with water and dried. After distilling off the solvent, the obtained brown oily residue was purified by column chromatography (silica gel, benzene:ethyl acetate=1:1). Thus 4.8 g of the title compound [compound 13] was obtained as a colorless viscous liquid.

$^1$H-NMR spectrum (60 MHz, CDCl$_3$) δ; 0.8~1.8(m,38H), 1.95(s,3H), 2.0(s,3), 2.05(s,3H), 2.5(t,2H), 4.6(broad s,8H), 7.2(m,3H), 8.2(m,3H), 8.6(m,3H), 9.0(m,3H)

IR (cm$^{-1}$ Liq.film); 1760, 1730 (O—CO—O, COOAr)

EXAMPLE 14

2-Methyl-2,3,4-tris(nicotinoyloxy)butyl 2,5,7,8-tetramethyl-2-(4',8',12'-trimethyltridecyl)-6-chromanyl carbonate [compound 14]

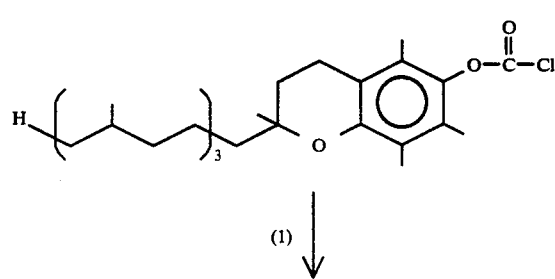

(1)

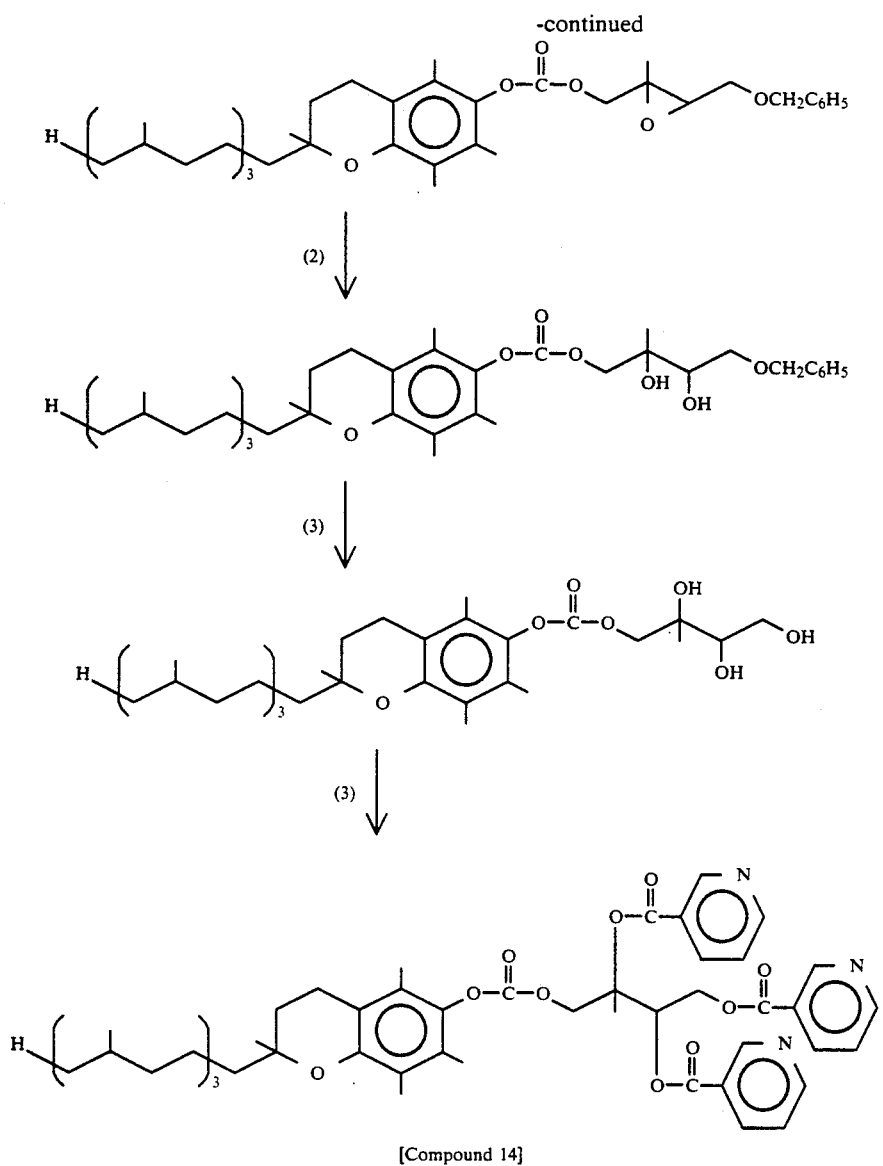

[Compound 14]

(1) Synthesis of 4-benzyloxy-2,3-epoxy-2-methylbutyl 2,5,7,8-tetramethyl-2-(4′,8′,12′-trimethyltridecyl)-6-chromanyl carbonate 4.2 g (0.02 mol) of 4-benzyloxy-2,3-epoxy-3-methylbutan-1-ol was dissolved in 50 ml of pyridine. To the obtained solution was added dropwise a solution of 11.0 g (0.02 mol) of o-tocopherol 6-chloroformate in 50 ml of ether within 30 minutes under ice-cooling and stirring. The mixture was further stirred under ice-cooling for 2 hours. Then the reaction mixture containing a precipitate of pyridine hydrochloride was poured into diluted hydrochloric acid and extracted with ether. The extract was washed with water and dried. After distilling off the solvent, the obtained oily residue was purified by column chromatography (silica gel, hexane/benzene). Thus 9.0 g of the title compound was obtained as a pale yellow, viscous liquid.

$^1$H-NMR spectrum (60 MHz, CDCl$_3$) $\delta$; 0.8~1.8(m,41H), 2.0(s,3H), 2.05(s,6H), 2.5(t,2H), 3.1(t,1H), 3.5(d,2H), 4.05(d,2H), 4.4(s,2H), 7.15(s,5H)

IR (cm$^{-1}$ Liq.film); 1760 (O—CO—O)

(2) Synthesis of 4-benzyloxy-2,3-dihydroxy-2-methylbutyl 2,5,7,8-tetramethyl-2-(4′,8′,12′-trimethyltridecyl)-6-chromanyl carbonate 8.6 g (0.013 mol) of 4-benzyloxy-2,3-epoxy-2-methylbutyl 2,5,7,8-tetramethyl-2-(4′,8′,12′-trimethyltridecyl)-6-chromanyl carbonate, 150 ml of tetrahydrofuran and 30 ml of water were mixed together. To the obtained mixture was slowly added dropwise a solution of 7 ml of 60% perchloric acid in 20 ml of water under ice-cooling and stirring. After the completion of the addition, the mixture was further stirred at the same temperature for 4 hours and then poured into water. After confirming that no peroxide remained therein with potassium iodide starch paper, the mixture was extracted with ether. The extract was washed with water and dried. After distilling off the solvent, the obtained oily residue was purified by column chromatography (silica gel, benzene:ethyl acetate=8:2). Thus 4.8 g of the title compound was obtained as a pale yellow, viscous liquid.

$^1$H-NMR$^{spectrum}$ (60 MHz, CDCl$_3$) δ; 8.8~1.8(m,41H), 2.0(s,3H), 2.05(s,6H), 2.5(t,2H), 3.0(broad,2H), 3.7~4.2(m,3H), 4.2(d,2H), 4.5(s,2H), 7.2(s,5H)

IR (cm$^1$ Liq.film); 1760 (O—CO—O), 3450 (OH)

(3) Synthesis of 2-methyl-2,3,4-tris(nicotinoyloxy)butyl 2,5,7,8-tetramethyl-2-(4′,8′,12′-trimethyltridecyl)-6-chromanyl carbonate 2.1 g of 4-benzyloxy-2,3-dihydroxy-2-methylbutyl 2,5,7,8-tetramethyl-2-(4′,8′,12′-trimethyltridecyl)-6-chromanyl carbonate, 0.3 g of 5% palladium carbon, 80 ml of ethanol and 8 ml of acetic acid were mixed together and the obtained mixture was catalytically reduced under a hydrogen pressure of 4 kg/cm$^2$. After the completion of the reaction, the catalyst was filtered off and the filtrate was poured into water. The oily matter thus separated out was extracted with ether. The extract was successively washed with an aqueous solution of sodium hydrogencarbonate and water, and dried. After distilling off the solvent, 1.3 g of a colorless oily residue was obtained. This product was confirmed as a single compound by thin layer chromatography and thus used in the subsequent step as such.

1.16 g (0.002 mol) of the 2,3,4-trihydroxy intermediate obtained in the above step and 2.2 g (0.012 mol) of nicotinoyl chloride hydrochloride were added to 50 ml of dichloromethane. To the obtained mixture was slowly added dropwise 3 g of triethylamine under ice-cooling and stirring. After the completion of the addition, the mixture was further stirred at room temperature for additional 4 hours. Then it was poured into water and extracted with dichloromethane. The extract was washed with water and dried. After distilling off the solvent, the obtained oily residue was purified by column chromatography (silica gel, hexane:ethyl acetate=2:1). Thus 1.3 g of the title compound [compound 14] was obtained as a colorless waxy product.

$^1$H-NMR$^{spectrum}$ (60 MHz, CDCl$_3$) δ; 0.8~1.8(m,41H), 1.95(s,3H), 2.0(s,6H), 2.45(t,2H), 4.5~6.0(m,4H), 6.1(t,1H), 7.2(m,3H), 8.2(m,3H), 8.6(m,3H), 9.0(m,3H)

IR (cm$^{-1}$ Liq.film); 1760, 1730 (O—CO—O, COOAr)

Example 15

3-Methyl-2,3,4-tris(nicotinoyloxy)butyl 2,5,7,8-tetramethyl-2-(4′,8′.12′-trimethyltridecyl)-6-chromanyl carbonate [Compound 15]

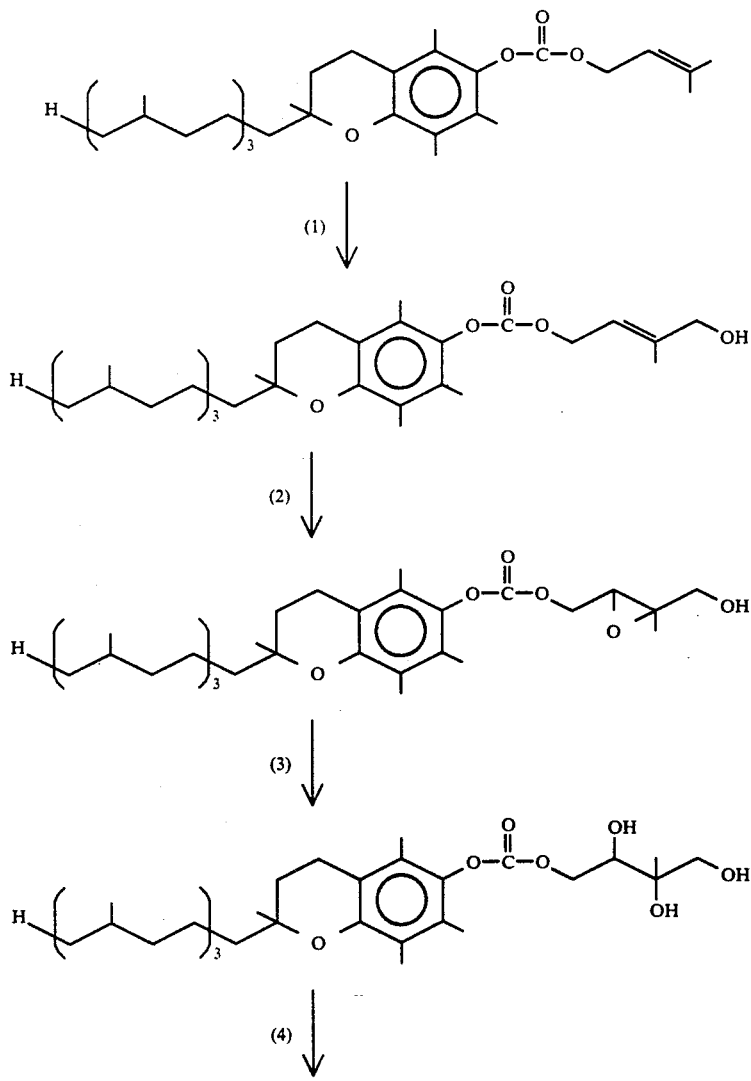

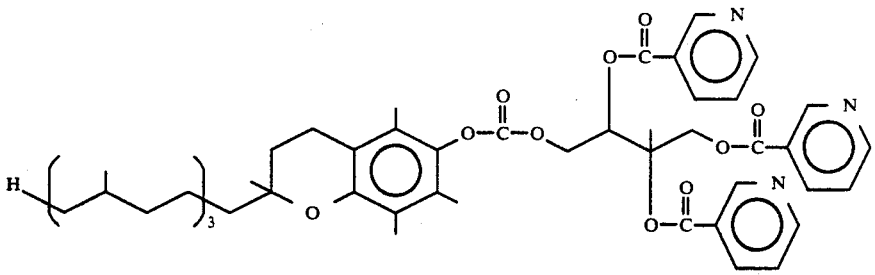

[Compound 15]

(1) Synthesis of 4-hydroxy-3-methyl-2-butenyl 2,5,7,8-tetramethyl-2-(4',8',12'-trimethyltridecyl)-6-chromanyl carbonate 10.8 g (0.02 mol) of the 3-methyl-2-butenyl 2,5,7,8-tetramethyl-2-(4',8',12'-trimethyltridecyl)-6-chromanyl carbonate obtained in Example 9 (1) and 6.6 g (0.06 mol) of selenium dioxide were added to 200 ml of ethanol and the obtained mixture was boiled under reflux for 4 hours with stirring. After cooling, the reaction mixture was filtered and the filtrate was poured into ice/water and extracted with ether. The extract was washed with water and dried. After distilling off the solvent, the obtained reddish orange, oily residue was purified by column chromatography (silica gel, hexane/ether). Thus 4.6 g of an aldehyde compound was obtained as a pale yellow, oily product.

4.3 g of the aldehyde compound obtained in the above step was dissolved in 50 ml of methanol. To the obtained solution was added 0.5 g of sodium borohydride under ice-cooling and stirring to thereby reduce the aldehyde. After the completion of the reaction, the reaction mixture was poured into water and extracted with ethyl acetate. The extract was washed with water and dried. After distilling off the solvent, 4.3 g of an oily residue was obtained. The obtained oily residue was purified by column chromatography (silica gel, benzene). Thus 4.2 g of the title compound was obtained as a colorless viscous liquid.

$^1$H-NMR$^{spectrum}$ (60 MHz, CDCl$_3$) δ; 0.8~1.8(m,41H), 1.95(s,3H), 2.0(s,3H), 2.02(s,3H), 2.45(t,2H), 3.0(broad,1H), 4.0(s,2H), 4.75(d,2H), 5.65(t,1H)

IR (cm$^{-1}$ Liq.film)); 1760 (O—CO—O), 3430 (OH)

(2) Synthesis of 2,3-epoxy-4-hydroxy-3-methylbutyl 2,5,7,8-tetramethyl-2-(4',8',12'-trimethyltridecyl)-6-chromanyl carbonate 4.1 g (0.0073 mol) of 4-hydroxy-3-methyl-2-butenyl 2,5,7,8-tetramethyl-2-(4',8',12'-trimethyltridecyl)-6-chromanyl carbonate was dissolved in 80 ml of dichloromethane. To the obtained solution was added 2.6 g (0.012 mol) of m-chloroperbenzoic acid (purity: 80%) in small portions under ice-cooling and stirring. After the completion of the addition, the obtained mixture was further stirred at the same temperature for 1 hour. After filtering off the precipitate thus formed, the filtrate was poured into an aqueous solution of sodium hydrosulfite and extracted with dichloromethane. The extract was washed with water and dried. After distilling off the solvent, the obtained oily residue was purified by column chromatography (silica gel, hexane/ethyl acetate).

Thus 4.0 g of the title compound was obtained as a colorless viscous liquid.

$^1$H-NMR$^{spectrum}$ (60 MHz, CDCl$_3$) δ; 0.8~1.8(m,41H), 2.0(s,3H), 2.1(s,6H), 2.5(t,2H), 2.9(broad,1H), 3.3(t,1H), 3.55(s,2H), 4.3(dd,2H)

IR (cm$^{-1}$ Liq.film); 1760 (O—CO—O), 3450 (OH)

(3) Synthesis of 2,3,4-trihydroxy-3-methylbutyl 2,5,7,8-tetramethyl-2-(4',8',12'-trimethyltridecyl)-6-chromanyl carbonate 5.8 g (0.01 mol) of 2,3-epoxy-4-hydroxy-3-methylbutyl 2,5,7,8-tetramethyl-2-(4',8',12'-trimethyltridecyl)-6-chromanyl carbonate, 200 ml of tetrahydrofuran and 50 ml of water were mixed together. To the obtained mixture was slowly added dropwise a solution of 10 ml of 60% perchloric acid in 10 ml of water under ice-cooling and stirring. After the completion of the addition, the mixture was further stirred under ice-cooling for 4 hours. After confirming that no peroxide remained therein with potassium iodide starch paper, the mixture was extracted with ether. The extract was washed with water and dried. After distilling off the solvent, the obtained oily residue was purified by column chromatography (silica gel, hexane:ethyl acetate=1:1). Thus 2.7 g of the title compound was obtained as a colorless viscous liquid.

$^1$H-NMR$^{spectrum}$ (60 MHz, CDCl$_3$) δ; 0.8~1.8(m,41H), 2.0(s,3H), 2.1(s,6H), 2.5(t,2H), 3.5~3.9(m,4H), 4.4(broad,3H), 4.7(t,1H)

IR (cm$^{-1}$ Liq.film); 1760 (O—CO—O), 3450 (OH)

(4) Synthesis of 3-methyl-2,3,4-tris(nicotinoyloxy)butyl 2,5,7,8l-tetramethyl-2-(4',8',12'-trimethyltridecyl)-6-chromanyl carbonate 2.6 g (0.0044 mol) of 2,3,4-trihydroxy-3-methylbutyl 2,5,7,8-tetramethyl-2-(4',8',12'-trimethyltridecyl)-6-chromanyl carbonate and 4.6 g (0.026 mol) of nicotinoyl chloride hydrochloride were added to 50 ml of dichloromethane. To the obtained mixture was slowly added dropwise 5.5 g of triethylamine under ice-cooling and stirring. After the completion of the addition, the mixture was further stirred at room temperature for 4 hours and then poured into water, followed by extracting with dichloromethane. The extract was washed with water and dried. After distilling off the solvent, the obtained oily residue was purified by column chromatography (silica gel, hexane:ethyl acetate=2:1). Thus 1.9 g of the title compound [compound 15] was obtained as a colorless waxy product.

$^1$H-NMR$^{spectrum}$ (60 MHz, CDCl$_3$) δ; 0.8~1.8(m,41H), 1.95(s,3H), 2.05(s,6H)), 2.45(t,2H), 4.3~4.7(m,5H), 7.2(m,3H), 8.1(m,3H), 8.6(m,3H), 9.1(m,3H)

IR (cm$^{-1}$ Liq.film); 1760, 1730 (O—CO—O, COOAr)

EXAMPLE 16

2,3,4,5-Tetrakis(nicotinoyloxy)pentyl 2,5,7,8-tetramethyl-2-(4',8-,12'-trimethyltridecyl)-6-chromanyl carbonate [Compound 16]

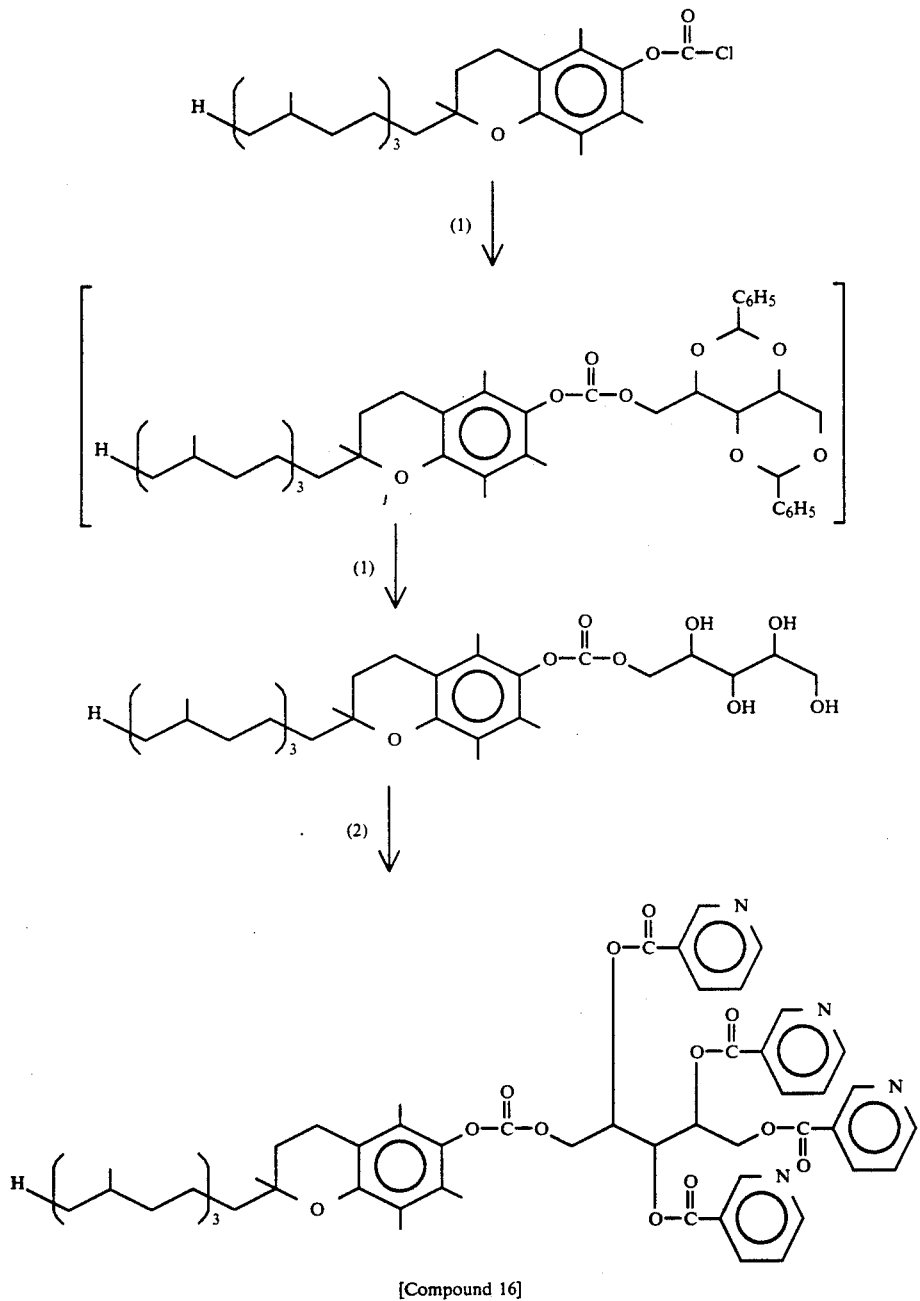

[Compound 16]

(1) Synthesis of 2,3,4,5-tetrahydroxypentyl 2,5,7,8-tetramethyl-2-(4',8',12'-trimethyltridecyl)-6-chromanyl carbonate 3.3 g (0.01 mol) of 2,3,4,5-dibenzylidenexylitol and 6 ml of pyridine were dissolved in 60 ml of dichloromethane. To the obtained solution was slowly added dropwise a solution of 5.0 g (0.01 mol) of α-tocopherol 6-chloroformate in 20 ml of dichloromethane under stirring at room temperature. Then the stirring was continued for additional 6 hours. The reaction mixture was poured into water and extracted with dichloromethane. The extract was successively washed with diluted hydrochloric acid and water, and dried. After distilling off the solvent, the obtained oily residue was purified by column chromatography (silica gel, benzene). Thus 2.9 g of a carbonate intermediate was obtained.

$^1$H-NMRspectrum (60 MHz, CDCl$_3$) δ; 0.8~1.8(m,38H), 1.95(s,3H), 2.0(s,6H), 2.48(t,2H), 3.6~4.55(m,7H), 5.42, 5.50(s×2,2H), 7.0~7.5(m,10H)

IR (cm$^1$ Liq.film); 1750 (O—CO—O)

2.25 g of the carbonate intermediate of 2,3,4,5-dibenzylidenexylitol obtained in the above step, 1.7 ml of trifluoroacetic acid and 0.7 ml of water were added to 50 ml of dichloromethane and stirred at room temperature for 5 hours. The reaction mixture was poured into water and extracted with dichloromethane. The extract was successively washed with an aqueous solution of sodium hydrogencarbonate and water, and dried. After distilling off the solvent, the obtained residue was purified by column chromatography (silica gel, ethyl acetate). Thus 1.2 g of the title compound was obtained as a colorless product.

$^1$H-NMR$^{spectrum}$ (60 MHz, CDCl$_3$) δ; 0.8~1.8(m,38H), 1.95(s,3H), 2.0(s,6H), 2.48(t,2H), 3.0~3.3(broad, 4H), 3.7~4.1(m,4H), 4.3(d,2H)

IR (cm$^{-1}$ Liq.film); 1758 (O—CO—O), 3440 (OH)

(2) Synthesis of 2,3,4,5-tetrakis(nicotinoyloxy)-pentyl 2,5,7,8-tetramethyl-2-(4′,8′,12′-trimethyltridecyl)-6-chromanyl carbonate 0.67 g (0.001 mol) of 2,3,4,5-tetrahydroxypentyl (4′,8′,12′-trimethyltridecyl)-6-chromanyl carbonate, 1.08 g (0.008 mol) of nicotinic acid, 2.6 g (0.008 mol) of 2-bromo-1-methylpyridinium iodide, 3.2 g (0.017 mol) of tri-n-butylamine and 20 ml of pyridine were mixed together and stirred for 8 hours under heating to 50° C. Then the reaction mixture was concentrated under reduced pressure. The obtained residue was dissolved in 200 ml of ethyl acetate, washed with water and dried. After distilling off the solvent, the obtained oily residue was purified by column chromatography (silica gel, ethyl acetate : methanol =98 : 2). Thus 0.7 g of the title compound [compound 16]was obtained as a colorless waxy product.

$^1$H-NMR$^{spectrum}$ (60 MHz, CDCl$_3$) δ; 0.8~1.8(m,38H), 1.95,1.99,2.05(s×3,9H), 2.5(t,2H), 4.5~4.8(m,4H)), 5.9(q,1H), 6.0(q,1H), 6.15 (m,1H), 7.3(m,4H), 8.25(m,4H), 8.75(m4H), 9.15(m,4H)

EXAMPLE 17

2,2-Bis(nicotinoyloxymethyl)butyl 2,5,7,8-tetramethyl-2-(4′,8′,12′-trimethyltridecyl)-6-chromanyl carbonate Compound 17]

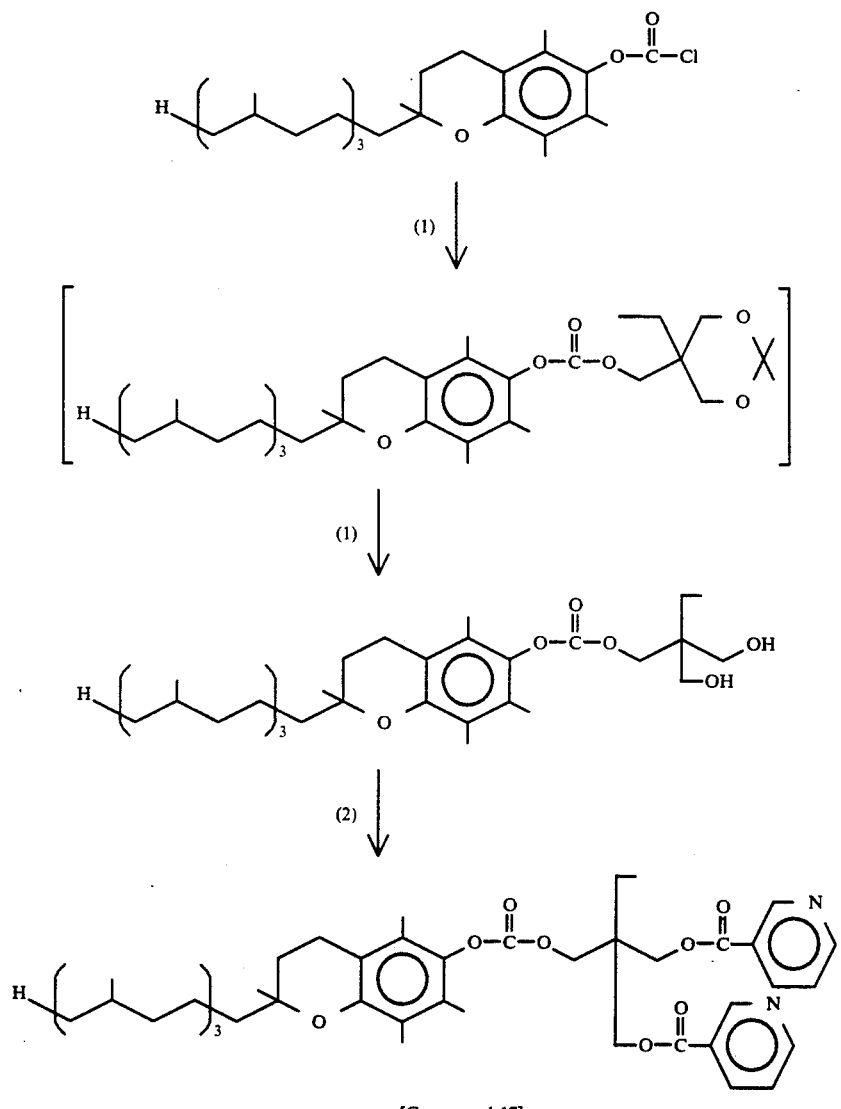

[Compound 17]

(1) Synthesis of 2,2-bis(hydroxymethyl)butyl 2,5,7,8-tetramethyl-2-(4′,8′,12′-trimethyltridecyl)-6-chromanyl carbonate To a mixture comprising 4.2 g (0.024 mol) of 5-ethyl-2-2-dimethyl-1,3-dioxan-5-ylmethanol, 14 ml of pyridine and 50 ml of dichloromethane was slowly added dropwise a solution of 9.8 g (0.02 mol) of α-tocopherol 6-chloroformate in 40 ml of dichloromethane under stirring at room temperature. After continuing the stirring for additional 6 hours, the reaction mixture was poured into water and extracted with dichloromethane. The extract was successively washed with diluted hydrochloric acid and water, and dried. After distilling off the solvent, 12.4 g of an oily residue was obtained.

10.0 g of the crude product of the carbonate intermediate obtained in the above step was added to a mixture comprising 70 ml of 2 N hydrochloric acid and 35 ml of methanol. Then the obtained mixture was heated under reflux for 6 hours. The reaction mixture was poured into 400 ml of water and the oily matter thus separated out was extracted with ethyl acetate. The extract was washed with water and dried. After distilling off the solvent, 8.7 g of an oily residue was obtained. The obtained residue was then purified by column chromatography (silica gel, hexane:ethyl acetate=7:3). Thus 6.0 g of the title compound was obtained as a colorless waxy product.

$^1$H-NMR$^{spectrum}$ (60 MHz, CDCl$_3$) δ; 0.8~1.8(m,43H), 1.95(s,3H), 2.0(s,6H), 2.5(t,2H), 2.8~3.0(d,2H), 3.5~4.7(d,4H), 4.3(s,2H)

IR (cm$^{-1}$ Liq.film); 1758 (O—CO—O), 3450 (OH)

(2) Synthesis of 2,2-bis(nicotinoyloxymethyl(butyl 2,5,7,8-tetramethyl-2-(4',8',12'-trimethyltridecyl)-6-chromanyl carbonate 6.0 g (0.01 mol) of 2,2-bis(hydroxymethyl)butyl 2,5,7,8-tetramethyl-2-(4',8',12'-trimethyltridecyl)-6-chromanyl carbonate and 7.2 g (0.04 mol) of nicotinoyl chloride hydrochloride were suspended in 85 ml of dichloromethane. To the obtained suspension was slowly added dropwise 8.1 g of triethylamine under ice-cooling and stirring. After stirring at room temperature for 5 hours, the reaction mixture was poured into water and extracted with ethyl acetate. The extract was washed with water and dried. After distilling off the solvent, the obtained oily residue was purified by column chromatography (silica gel, chloroform). Thus 5.5 g of the title compound [compound 17] was obtained as a colorless waxy product.

$^1$H-NMR$^{spectrum}$ (60 MHz, CDCl$_3$) δ; 0.8~1.8(m,43H), 1.95,2.00,2.05(s×3.9H), 2.5(t,2H), 4.35(s,2H), 4.4(s,4H), 7.4(m,2H), 8.3(m,2H), 8.75(m,2H), 9.2(m,2H)

IR (cm$^{-1}$ Liq.film); 1760, 1730 (O—CO—O, COOAr)

EXAMPLE 18

4-Nicotinoyloxy-3,3-bis(nicotinoyloxymethyl)butyl 2,5,7,8-tetramethyl-2-(4',8',12'-trimethyltridecyl)-6-chromanyl carbonate [Compound 18]

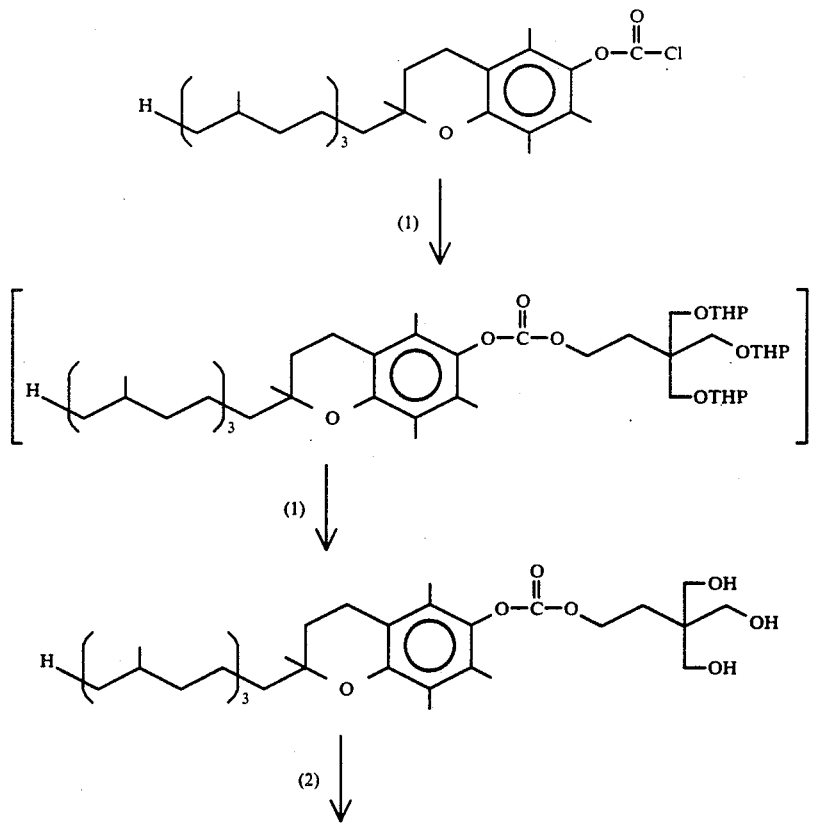

-continued

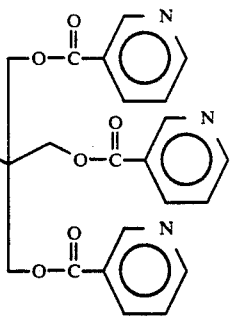

[Compound 18]

(1) Synthesis of 4-hydroxy-3,3-bis(hydroxymethyl)-butyl 2,5,7,8-tetramethyl-2-(4',8',12'-trimethyltridecyl)-6-chromanyl carbonate To a mixture comprising 4.0 g (0.01 mol) of 4-hydroxy-3,3-bis(hydroxymethyl)butan-1-ol, 5.2 g (0.011 mol) of o-tocopherol 6-chloroformate and 30 ml of ether was slowly added dropwise a solution of 1.0 g of pyridine in 10 ml of ether under ice-cooling and stirring. After stirring for additional 6 hours at room temperature, the reaction mixture was poured into water and extracted with ether. The extract was successively washed with diluted hydrochloric acid and water, and dried. After distilling off the solvent, 9.5 g of an oily residue was obtained.

A mixture comprising 2.7 g of the crude product of the carbonate intermediate obtained in the above step, 0.5 g of p-toluenesulfonic acid and 50 ml of methanol was stirred at room temperature for 2 hours. Then the reaction mixture was concentrated under reduced pressure. After distilling off the methanol, water was added thereto and the oily matter thus separated out was extracted with ether. The extract was washed with water and dried. After distilling off the solvent, 2.3 g of an oily residue was obtained. The oily residue was then purified by column chromatography (silica gel, chloroform/methanol). Thus 1.7 g of the title compound was obtained as a colorless waxy product.

$^1$H-NMRspectrum (60 MHz, CDCl$_3$) $\delta$; 0.8~1.8(m,40H), 2.00(s,3H), 2.05(s,6H), 2.45(m,2H), 3.2~3.7(m,9H), 4.25(t,2H)

IR (cm$^{-1}$ Liq.film); 1750 (O—CO—O), 3500 (OH)

(2) Synthesis of 4-nicotinoyloxy-3,3-bis(nicotinoyloxymethyl)butyl 2,5,7,8-tetramethyl-2-(4',8',12,-trimethyltridecyl)-6-chromanyl carbonate A suspension comprising 1.0 g (0.002 mol) of 4-hydroxy-3,3-bis(hydroxymethyl)butyl 2,5,7,8-tetramethyl-2-(4',8',12'-trimethyltridecyl)-6-chromanyl carbonate, 1.2 g (0.012 mol) of nicotinic acid, 3.0 g (0.012 mol) of 1-methyl-2-bromopyridinium iodide, 3.7 g (0.024 mol) of tri-n-butylamine and 25 ml of pyridine was heated to 50° C and stirred for 5 hours. The reaction mixture was concentrated under reduced pressure and water was added to the residue. The oily matter thus separated out was extracted with ethyl acetate. The extract was washed with water and dried. After distilling off the solvent, an oily residue was obtained. The obtained brown oily residue was purified by column chromatography (silica gel, benzene:ethyl acetate=3:7). Thus 0.9 g of the title compound [Compound 18] was obtained as a colorless waxy product. $^1$H-NMR$^{spectrum}$ (60 MHz, CDCl$_3$) $\delta$; 0.8~1.8(m,40H), 1.96,2.00,2.05(s×3,9H), 2.5(t,2H), 4.5(t,2H), 4.60(s,6H), 7.35(m,3H), 8.3(m,3H), 8.8(m,3H), 9.32(m,3H)

IR (cm$^{-1}$ Liq.film); 1755, 1730 (O—CO—O, COOAr)

Effects of the Invention

To further illustrate the effects of the present invention, the following Test Examples will be given.

EXPERIMENTAL EXAMPLE 1

Lipid level-lowering effect on Triton-induced hyperlipemic rat

Method

The effect of the invention compound (2) in lowering the lipid level of Triton-induced hyperlipemic rats was examined in accordance with a method reported by Schur et al. [Schur et al., Lipid, 7, 68 (1972)].

Male Sprague Dawley rats weighing 253 to 290 g were used, and 300 mg/kg of a solution of Triton WR-1339 in physiological saline was intravenously injected into the tail vein of each animal. Immediately after the injection, the invention compound (2), which had been dissolved in cottonseed oil, was orally administered to the animals in doses of 38.0, 94.9 and 237.2 mg/kg. Then the animals were fasted and the blood was sampled 9 hours after the administration to measure the total serum cholesterol level and serum triglyceride level. Each group consisted of 7 rats.

To a control group was given 1 ml/kg of cottonseed oil in the same manner.

Results

Table 1 shows the effects of the invention compound (2) in lowering the lipid level of the Triton-induced hyperlipemic rats compared with the data of the control group.

As Table 1 shows, both of the total serum cholesterol and serum triglyceride levels were significantly lowered.

TABLE 1

| Dose (mg/kg) | Decrease in lipid level compared with control group | |
|---|---|---|
| | Total serum cholesterol | Serum triglyceride |
| 38.0 | 13.2 ± 2.8 | 19.2 ± 2.9 |
| 94.9 | 21.5 ± 1.9 | 42.7 ± 3.3 |
| 237.2 | 24.4 ± 3.6 | 47.5 ± 3.5 |

Each value represents "mean ±standard deviation".

EXPERIMENTAL EXAMPLE 2

Effect of lowering free fatty acids in rat plasma

Method

The invention compounds (1), (2) and (3) were dissolved in cottonseed oil and orally administered to male Sprague Dawley rats weighing 300 g in such a manner as to give each invention compound in an amount corresponding to 0.5 mmol of nicotinic acid per kg body weight per ml.

After the administration, 0.5-ml portions of the blood of each animal were sampled from the tail vein with the lapse of time and thus the level of free fatty acids contained in the plasma was monitored by the ACS-ACOD method (NEFA C-Test, mfd. by Wako Pure Chemical Industry Co.).

For comparison, α-tocopheryl nicotinate and niceritrol were orally administered in the same manner.

Results

Table 2 shows changes in the plasma free fatty acid lowering ratios achieved with the use of the invention compounds (1), (2) and (3) with the lapse of time compared with the data of the comparative groups.

Table 2 clearly shows that the invention compounds effectively lowered the free fatty acid level in plasma.

TABLE 2

| Test compound | Dose (mg/kg) | Free fatty acid lowering ratio (%) after | | | |
|---|---|---|---|---|---|
| | | 1 hr | 2 hr | 3 hr | 4 hr |
| niceritrol | 70 | 59 ± 1 | 56 ± 10 | 71 ± 2 | 15 ± 23 |
| α-tocopheryl nicotinate | 268 | 46 ± 5 | 54 ± 4 | 51 ± 12 | 24 ± 14 |
| invention compound (1) | 190 | 62 ± 1 | 57 ± 5 | 64 ± 3 | 33 ± 33 |
| invention compound (2) | 190 | 76 ± 3 | 75 ± 2 | 60 ± 6 | 53 ± 14 |
| invention compound (3) | 193 | 58 ± 6 | 64 ± 3 | 64 ± 1 | 17 ± 26 |

Each value represents "mean ±standard deviation".

EXPERIMENTAL EXAMPLE 3

Change in plasma nicotinic acid level in rat upon oral administration

Method

The invention compounds (2) and (5) were dissolved in cottonseed oil and orally administered to male SD rats weighing 280 to 350 g, which were fed ad libitum, in such a manner as to give each invention compound in an amount corresponding to 0.5 mmol of nicotinic acid per kg body weight per ml.

After the administration, the blood of each animal was sampled with the lapse of time and thus plasma samples were prepared. The nicotinic acid level in a plasma sample was determined by high performance liquid chromatography under the conditions as specified below [Suzuki et al., Vitamin, 60, 272 1986)].

For comparison, nicotinic acid was orally given in the same manner, namely, in an amount corresponding to 0.5 mmol of nicotinic acid per kg body weight per ml. Then the nicotinic acid level in the plasma was determined in the same manner as the one described above. Isonitotinic acid was employed as an internal standard.

High performance liquid chromatography:
Device: Shimadzu LC-6A
stationary phase: Shim-Pack CLC-ODS.
mobile phase: 10 mM sodium phosphate buffer (pH 2.1), 10 mM sodium 1-octane-sulfonate and 5% acetonitrile.
temperature: 4° C.
flow rate: 2.0 ml/min.
detection wavelength: 254 nm.

Results

FIG. 1 shows changes in plasma nicotinic acid level wherein each data represents the mean ±standard deviation of 3 or 4 samples.

As FIG. 1 shows, the changes in nicotinic acid level caused by the administration of the invention compounds (2) and (5) proceed slowly, compared with the comparative case wherein nicotinic acid was administered, suggesting that the invention compounds were slowly released into the plasma with the lapse of time.

EXPERIMENTAL EXAMPLE 4

Change in plasma vitamin E level of rat upon oral administration

Method

The invention compound (2) was dissolved in cottonseed oil and orally administered to male SD rats weighing 280 to 350 g in such a manner as to give each invention compound in an amount corresponding to 0.25 mmol of nicotinic acid per kg body weight per ml.

After the administration, the blood of each animal was sampled with the lapse of time and the vitamin E level in plasma was determined by high performance liquid chromatography [Abe et al., Vitamin, 49, 259 (1975)].

As a control, cottonseed oil was orally administered in the same manner and the vitamin E level was determined.

Results

Figure 2:
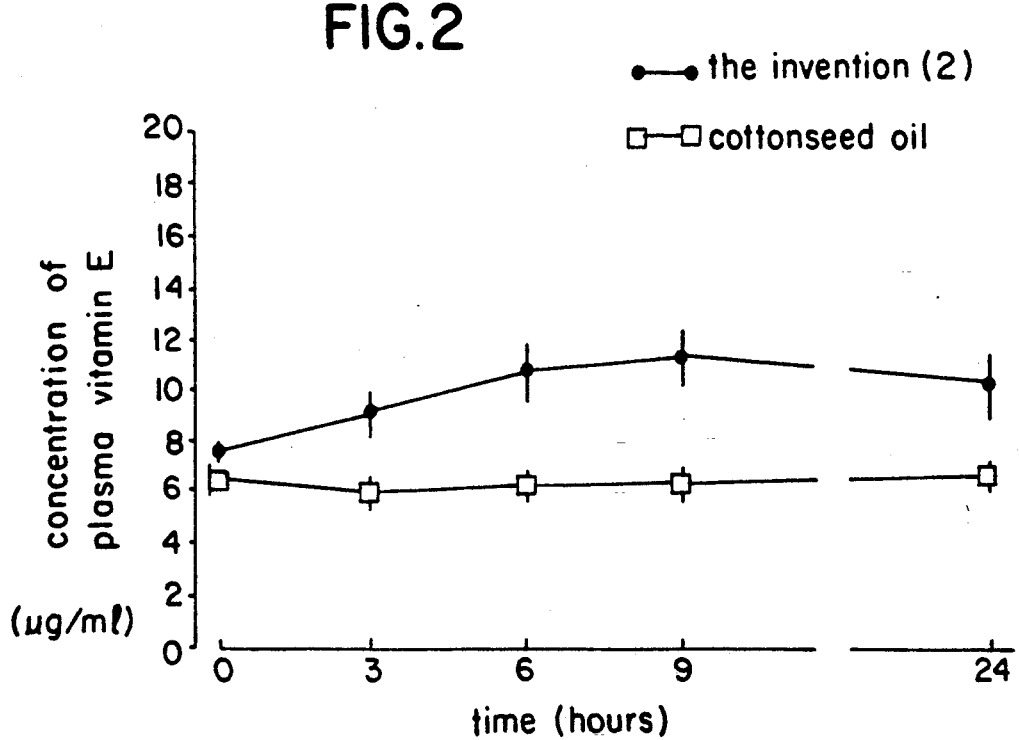
FIG. 2 shows changes in plasma vitamin E levels after administering the invention compound (2).

FIG. 2 shows changes in plasma vitamin E levels wherein each data represents the mean± standard deviation of a group consisting of 4 animals.

As FIG. 2 shows, the invention compound (2) showed good migration of vitamin E into the plasma.

The results of these Experimental Examples 1 to 4 indicate that the compounds of the present invention sustain an excellent antihyperlipemic effect of nicotinic acid while relieving the side effects thereof, for example, rubor or itching, by slowly releasing nicotinic acid. Since vitamin E is effective in lowering lipid level, the compounds of the present invention are useful as a remedy for arteriosclerosis which sustains the basic pharmacological effects of both of vitamin E and nicotinic acid, namely, improving circulation and lipid metabolism, while relieving the side effects of nicotinic acid.

We claim:

1. A vitamin E derivative represented by the following general formula (I):

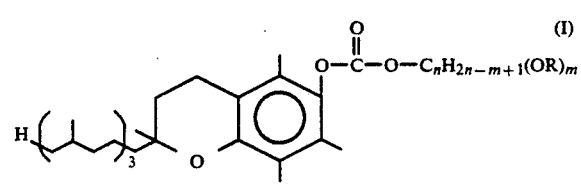

wherein R represents a nicotinoyl group; and m is an integer of from 2 to 5 while n is an integer of from 3 to 6, provided that n is larger than m.

2. A pharmaceutical composition comprising a Pharmacologically effective amount of the vitamin E derivative as defined in claim 1 and a pharmacologically acceptable carrier.

3. A method for treating arteriosclerosis by administering a pharmacologically effective amount of the vitamin E derivative as defined in claim 1 to a human patient.

* * * * *